US010783387B2

(12) United States Patent
Jung et al.

(10) Patent No.: US 10,783,387 B2
(45) Date of Patent: Sep. 22, 2020

(54) BIOMETRIC INFORMATION SENSOR AND DISPLAY DEVICE HAVING THE SAME

(71) Applicant: SAMSUNG DISPLAY CO., LTD., Yongin-si, Gyeonggi-do (KR)

(72) Inventors: Han Yung Jung, Yongin-si (KR); Chaun Gi Choi, Yongin-si (KR)

(73) Assignee: SAMSUNG DISPLAY CO., LTD., Yongin-si, Gyeonggi-Do (KR)

(*) Notice: Subject to any disclaimer, the term of this patent is extended or adjusted under 35 U.S.C. 154(b) by 109 days.

(21) Appl. No.: 16/107,104

(22) Filed: Aug. 21, 2018

(65) Prior Publication Data
US 2019/0251378 A1 Aug. 15, 2019

(30) Foreign Application Priority Data
Feb. 14, 2018 (KR) .................. 10-2018-0018190

(51) Int. Cl.
G06K 9/00 (2006.01)
G01H 11/08 (2006.01)
A61B 5/1172 (2016.01)
G01S 1/72 (2006.01)

(52) U.S. Cl.
CPC ........ *G06K 9/00885* (2013.01); *A61B 5/1172* (2013.01); *G01H 11/08* (2013.01); *G01S 1/72* (2013.01); *G06K 9/0002* (2013.01)

(58) Field of Classification Search
CPC .... G06K 9/00885; G06K 9/0002; G01S 1/72; A61B 5/1172; A61B 2562/046; A61B 2562/125; A61B 2562/0247; G01H 11/08; B06B 1/0629; B06B 2201/70; B06B 1/0207
See application file for complete search history.

(56) References Cited

U.S. PATENT DOCUMENTS

| 4,835,747 | A | 5/1989 | Billet |
| 7,067,962 | B2 | 6/2006 | Scott |
| 7,196,970 | B2 | 3/2007 | Moon et al. |
| 7,400,750 | B2 | 7/2008 | Nam |
| 9,946,914 | B1* | 4/2018 | Kitchens, II ......... G06K 9/0002 |
| 10,140,534 | B2* | 11/2018 | Kitchens, II ......... A61B 8/0858 |
| 10,262,178 | B2* | 4/2019 | Sun ...................... G06K 9/0002 |
| 2015/0015515 | A1 | 1/2015 | Dickinson et al. |
| 2017/0090024 | A1* | 3/2017 | Kitchens, II ......... A61B 8/0858 |
| 2018/0189539 | A1* | 7/2018 | Chen ...................... G06F 3/043 |

(Continued)

FOREIGN PATENT DOCUMENTS

| KR | 1020070101244 | 10/2007 |
| KR | 1020160030968 | 3/2016 |

(Continued)

Primary Examiner — John B Strege
(74) Attorney, Agent, or Firm — F. Chau & Associates, LLC

(57) ABSTRACT

A biometric information sensor includes a first substrate and a first sensor electrode disposed on the first substrate. A second sensor electrode is disposed on the first substrate at a same distance from the first substrate as the first sensor electrode. The second sensor electrode is spaced apart from the first sensor electrode. A piezoelectric layer is disposed between the first sensor electrode and the second sensor electrode. A second substrate is disposed on the first sensor electrode, the second sensor electrode, and the piezoelectric layer.

26 Claims, 12 Drawing Sheets

(56) References Cited

U.S. PATENT DOCUMENTS

| | | | |
|---|---|---|---|
| 2018/0196982 A1* | 7/2018 | Panchawagh | G06K 9/00073 |
| 2018/0335868 A1 | 11/2018 | Jung et al. | |
| 2018/0373913 A1* | 12/2018 | Panchawagh | G06K 9/0002 |
| 2019/0026520 A1* | 1/2019 | Park | H01L 41/43 |
| 2019/0122018 A1* | 4/2019 | Kho | H04R 7/045 |

FOREIGN PATENT DOCUMENTS

| | | |
|---|---|---|
| KR | 101730842 | 4/2017 |
| KR | 10-2018-0126135 | 11/2018 |

\* cited by examiner

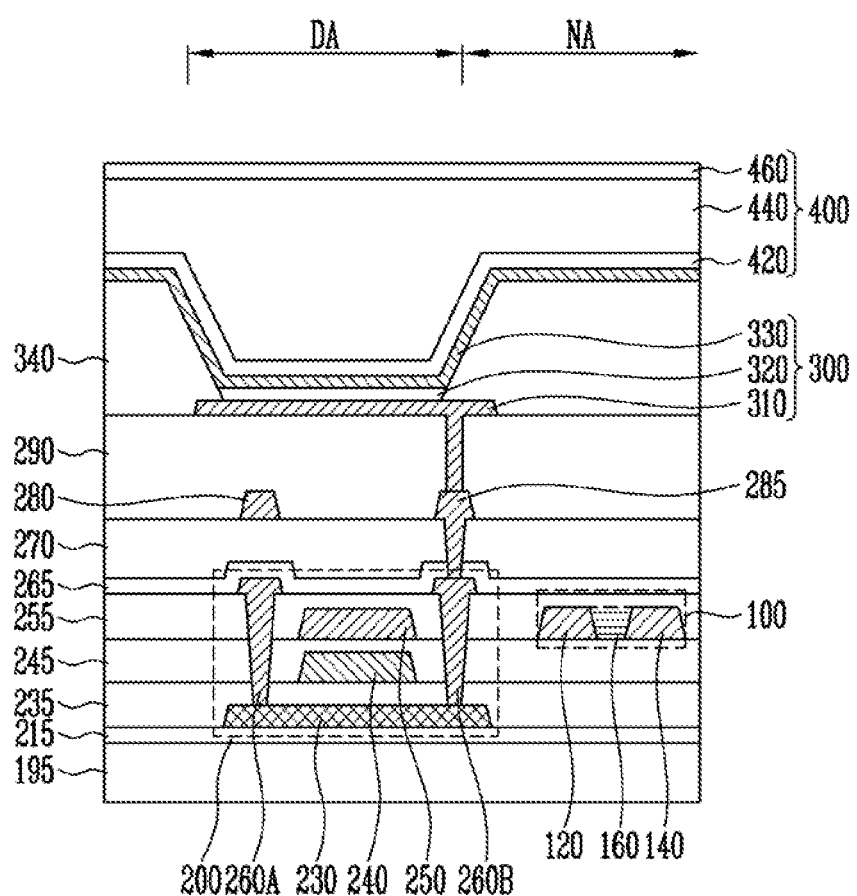

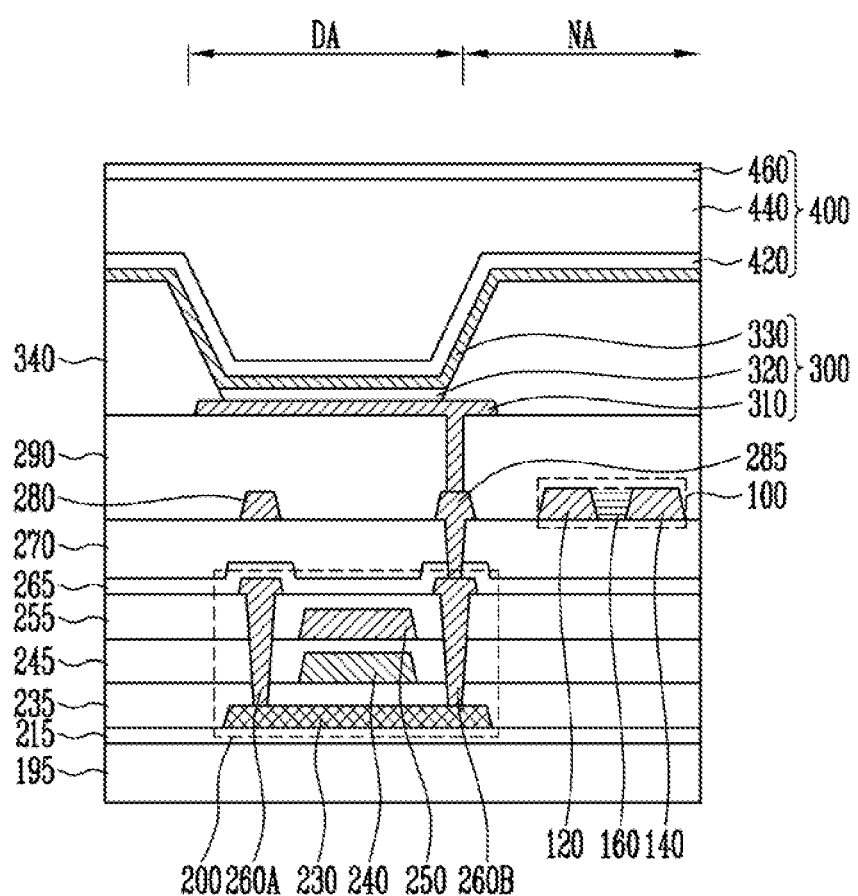

BIOMETRIC INFORMATION SENSOR AND DISPLAY DEVICE HAVING THE SAME

CROSS REFERENCE TO RELATED APPLICATION

This application claims priority under 35 U.S.C. § 119 to Korean Patent Application No. 10-2018-0018190, filed on Feb. 14, 2018 in the Korean Intellectual Property Office (KIPO), the disclosure of which is incorporated by reference herein in its entirety.

1. TECHNICAL FIELD

Exemplary embodiments of the present invention relate to a biometric information sensor, and more particularly, to a display device having the same.

2. DISCUSSION OF RELATED ART

Accurate user authentication has become a necessary procedure to gain access to personal or secured data in personal devices or in making financial transactions.

User authentication technology suitable for personal devices includes use of unique biometric information such as fingerprints and iris recognition.

SUMMARY

An exemplary embodiment of the present invention provides de an ultrasonic biometric information sensor including sensor electrodes disposed on a same layer as each other.

An exemplary embodiment of the present invention provides a display device including the biometric information sensor.

According to an exemplary embodiment of the present invention, a biometric information sensor includes a first substrate and a first sensor electrode disposed on the first substrate. A second sensor electrode is disposed on the first substrate at a same distance from the first substrate as the first sensor electrode. The second sensor electrode is spaced apart from the first sensor electrode. A piezoelectric layer is disposed between the first sensor electrode and the second sensor electrode. A second substrate is disposed on the first sensor electrode, the second sensor electrode, and the piezoelectric layer.

In an exemplary embodiment of the present invention, the piezoelectric layer may cover at least a portion of an upper surface of the first sensor electrode and at least a portion of an upper surface of the second sensor electrode.

In an exemplary embodiment of the present invention, heights of the piezoelectric layer, the first sensor electrode, and the second sensor electrode above the first substrate may be substantially the same as each other.

In an exemplary embodiment of the present invention, charge transfer may occur between the first sensor electrode and the second sensor electrode along a first direction parallel to an upper surface of the first substrate when a pressure is applied in a second direction orthogonal to the upper surface of the first substrate.

In an exemplary embodiment of the present invention, the first sensor electrode, the second sensor electrode, and the piezoelectric layer may form an ultrasonic transmitter generating an ultrasonic wave in response to an ultrasonic wave generating signal or may form an ultrasonic receiver generating a detection signal in response to a reflection of the ultrasonic wave.

In an exemplary embodiment of the present invention, the first sensor electrode may be electrically connected to a common voltage. The second sensor electrode may be electrically connected to a conduction line transmitting the ultrasonic wave generating signal or receiving a detection signal.

In an exemplary embodiment of the present invention, a planarization layer may be disposed between the first sensor electrode, the second sensor electrode, and the piezoelectric layer and the second substrate to at least partially cover the first sensor electrode, the second sensor electrode, and the piezoelectric layer.

In an exemplary embodiment of the present invention, a third sensor electrode may be disposed on the first substrate at a same distance from the first substrate as the first sensor electrode and spaced apart from the first and second sensor electrodes. A fourth sensor electrode may be disposed on the piezoelectric layer to overlap the third sensor electrode. The piezoelectric layer may cover substantially an entire upper surface of the third sensor electrode.

In an exemplary embodiment of the present invention, when a pressure is applied in a direction orthogonal to an upper surface of the first substrate facing the second substrate, charge transfer may occur in a direction parallel to the upper surface of the first substrate between the first sensor electrode and the second sensor electrode. Charge transfer may occur in the direction orthogonal to the upper surface of the first substrate between the third sensor electrode and the fourth sensor electrode, when the pressure is applied.

According to an exemplary embodiment of the present invention, a display device includes a substrate and a fingerprint sensor array disposed on the substrate. The fingerprint sensor array includes a plurality of fingerprint sensors having an ultrasonic transmitter and an ultrasonic receiver. An insulation layer is disposed on the fingerprint sensor array. A semiconductor element is disposed on the insulation layer. A pixel structure is disposed on the semiconductor element. An encapsulation layer is disposed on the pixel structure. The fingerprint sensor array includes a first sensor electrode disposed on the substrate. A second sensor electrode is disposed on the substrate at a same distance from the substrate as the first sensor electrode. The second sensor electrode is spaced apart from the first sensor electrode. A piezoelectric layer is disposed between the first sensor electrode and the second sensor electrode.

In an exemplary embodiment of the present invention, the first sensor electrode may be electrically connected to a common voltage. The second sensor electrode may be electrically connected to a conduction line transmitting an ultrasonic wave generating signal or receiving a detection signal.

In an exemplary embodiment of the present invention, the piezoelectric layer may cover at least a portion of an upper surface of the first sensor electrode and at least a portion of an upper surface of the second sensor electrode.

In an exemplary embodiment of the present invention, a distance between the first sensor electrode and the second sensor electrode may be shorter than a shortest distance between adjacent fingerprint sensors of the plurality of fingerprint sensors.

In an exemplary embodiment of the present invention, at least one fingerprint sensor of the plurality of fingerprint sensors may operate as an ultrasonic transmitter to generate an ultrasonic wave when the ultrasonic wave generating signal is transferred through the second sensor electrode.

In an exemplary embodiment of the present invention, at least one fingerprint sensor of the plurality of fingerprint sensors may operate as an ultrasonic receiver to generate an ultrasonic wave when the ultrasonic wave generating signal is not transferred through the second sensor electrode.

In an exemplary embodiment of the present invention, the pixel structure may include an organic light emitting layer. The pixel structure may include a light emitting area in a position corresponding to the organic light emitting layer and a non-light emitting area adjacent to the light emitting area. Each of the fingerprint sensors may overlap the non-light emitting area.

In an exemplary embodiment of the present invention, a second plurality of fingerprint sensors may have substantially a same configuration as the plurality of fingerprint sensors. The second plurality of fingerprint sensors are arranged with the semiconductor element above the plurality of fingerprint sensors. The second plurality of fingerprint sensors might not overlap the fingerprint sensor array.

According to an exemplary embodiment of the present invention, a display device includes a substrate and a semiconductor element disposed on the substrate. A first sensor electrode is disposed on the substrate. A second sensor electrode is disposed on the substrate at a same distance from the substrate as the first sensor electrode. A piezoelectric material is between the first sensor electrode and the second sensor electrode. A pixel structure is disposed on the semiconductor element. The pixel structure includes a light emitting area and a non-light emitting area adjacent to the light emitting area. An encapsulation layer is disposed on the pixel structure. The first sensor electrode, the second sensor electrode, and the piezoelectric material form a fingerprint sensor.

In an exemplary embodiment of the present invention, the fingerprint sensor may overlap the non-light emitting area.

In an exemplary embodiment of the present invention, the first sensor electrode may be electrically connected to a conduction line transmitting a common voltage. The second sensor electrode may be electrically connected to a conduction line transmitting an ultrasonic wave generating signal or a detection signal.

According to an exemplary embodiment of the present invention, a biometric information sensor includes a first substrate and a first sensor electrode disposed on the first substrate. A second sensor electrode is disposed on the first substrate at a same distance from the first substrate as the first sensor electrode, wherein the second sensor electrode is spaced apart from the first sensor electrode along a direction parallel to an upper surface of the first substrate facing the first sensor electrode. A piezoelectric layer is in direct contact with at least one surface of the first sensor electrode and at least one surface of the second sensor electrode. A second substrate is disposed on the first sensor electrode, the second sensor electrode, and the piezoelectric layer.

In an exemplary embodiment of the present invention, the piezoelectric layer may be in direct contact with a side of the first sensor electrode and a side of the second sensor electrode opposite to the side of the first sensor electrode.

In an exemplary embodiment of the present invention, the piezoelectric layer may cover at least a portion of an upper surface of the first sensor electrode and at least a portion of an upper surface of the second sensor electrode.

In an exemplary embodiment of the present invention, the piezoelectric layer may be integrally formed on an upper surface of the first sensor electrode and an upper surface of the second sensor electrode.

In an exemplary embodiment of the present invention, a third sensor electrode may be disposed on the first substrate at a same distance from the first substrate as the first sensor electrode. The third sensor electrode is spaced apart from the first and second sensor electrodes. A fourth sensor electrode is disposed on the piezoelectric layer.

In an exemplary embodiment of the present invention, the fourth sensor electrode may overlap the third sensor electrode.

In an exemplary embodiment of the present invention, a third sensor electrode may be disposed on the piezoelectric layer not to overlap with the first and second sensor electrodes. A fourth sensor electrode may be disposed on the piezoelectric layer and may be spaced apart from the third sensor electrode. The fourth sensor electrode might not be overlapped with the first and second sensor electrodes. Charge transfer may occur between the first sensor electrode and the third sensor electrode and between the second sensor electrode and the fourth sensor electrode along a first direction parallel to an upper surface of the first substrate when a pressure is applied in a second direction orthogonal to the upper surface of the first substrate.

In an exemplary embodiment of the present invention, the piezoelectric layer may be disposed between the first substrate and the first and second sensor electrodes. The piezoelectric layer may be in direct contact with a lower surface of each of the first and second sensor electrodes.

According to an exemplary embodiment of the present invention, a display device includes a first substrate and a biometric information sensor disposed on the first substrate. The biometric information sensor includes a first fingerprint sensor and a second fingerprint sensor spaced apart from the first fingerprint sensor. The first fingerprint sensor includes a first sensor electrode in direct contact with the first substrate and a second sensor electrode in direct contact with the first substrate and spaced apart from the first sensor electrode. The second fingerprint sensor includes a third sensor electrode in direct contact with the first substrate and a fourth sensor electrode in direct contact with the first substrate and spaced apart from the third sensor electrode. A piezoelectric layer is disposed on the first substrate between the first and second sensor electrodes and between the third and fourth sensor electrodes. A second substrate is disposed on the piezoelectric layer.

In an exemplary embodiment of the present invention, the second sensor electrode may be positioned at a same distance from the first substrate as the first sensor electrode.

In an exemplary embodiment of the present invention, the first sensor electrode, the second sensor electrode, and the piezoelectric layer may form an ultrasonic receiver receiving a reflection of the ultrasonic wave to generate a detection signal.

In an exemplary embodiment of the present invention, a distance between the first and second sensor electrodes may be smaller than a distance between the first fingerprint sensor and the second fingerprint sensor.

BRIEF DESCRIPTION OF THE DRAWINGS

The above and other features of the present invention will become more apparent by describing in detail exemplary embodiments thereof with reference to the accompanying drawings, in which:

FIGS. 11A, 11B, 11C and 11D are each cross-sectional views illustrating an example of the display device of FIG. 1.

DETAILED DESCRIPTION OF EMBODIMENTS

Figure 1:
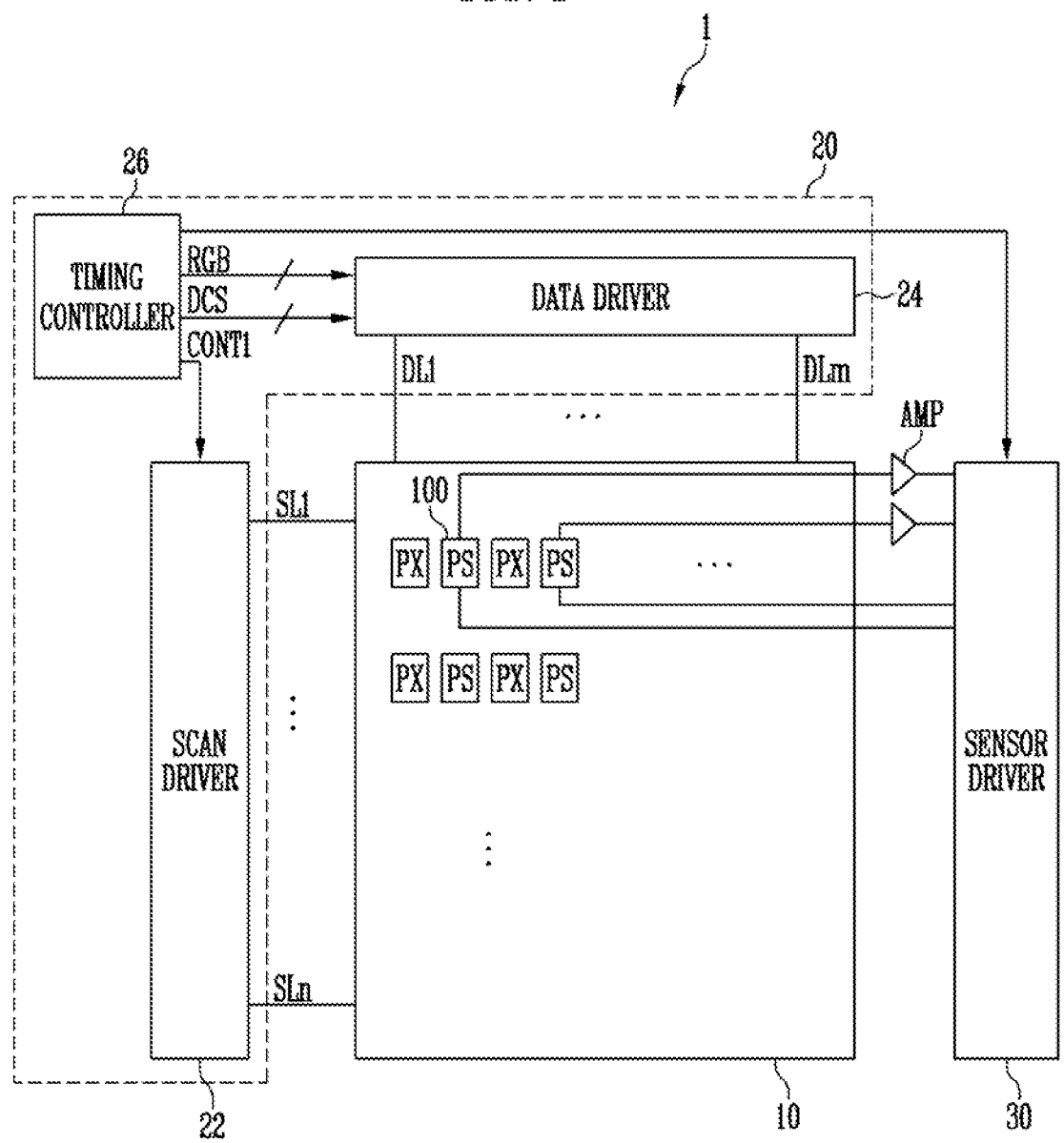
FIG. 1 is a block diagram of a display device according to an exemplary embodiment of the present invention.

Exemplary embodiments of the present invention will be described below in more detail with reference to the accompanying drawings. In this regard, the exemplary embodiments may have different forms and should not be construed as being limited to the exemplary embodiments of the present invention described herein. Like reference numerals may refer to like elements throughout the specification and drawings.

It will be understood that although the terms "first" and "second" may be used herein to describe various components, these components should not be limited by these terms.

Figure 2:
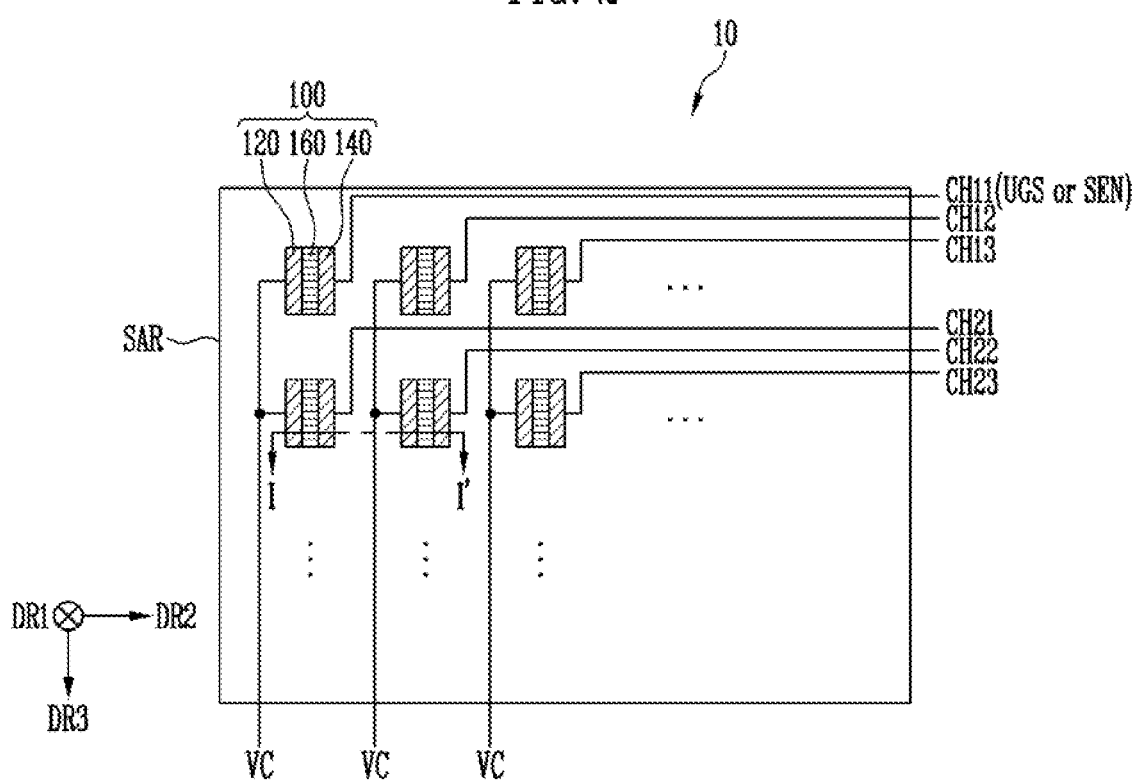
FIG. 2 is a plan view of an example of a fingerprint sensor array included in the display device of FIG. 1.

FIG. 1 is a block diagram of a display device according to an exemplary embodiment of the present invention. FIG. 2 is a plan view of an example of a fingerprint sensor array included in the display device of FIG. 1.

Referring to FIGS. 1 and 2, a display device 1 may include a display panel 10, a sensor array SAR, a display driver 20, and a sensor driver 30. In an exemplary embodiment of the present invention, the sensor array SAR may be disposed above or below the display panel 10 (e.g., along a direction orthogonal to an upper surface of the display panel 10), or may be integrated in the display panel 10.

The display device 1 may be an organic light emitting display device, or a liquid crystal display device. The display device 1 may be a flat display device, a flexible display device, a curved display device, a foldable display device, or a bendable display device. The display device 1 may be a transparent display device, a head-mounted display device, or a wearable display device; however, exemplary embodiments of the present invention are not limited thereto.

The display panel 10 may include a plurality of scan lines SL1 to SLn and a plurality of data lines DL1 to DLm and may further include a plurality of pixels PX connected to the scan lines SL1 to SLn and the data lines DL1 to DLm, where n and m are integers greater than 1. The pixels PX may be arranged in a matrix form. The plurality of scan lines SL1 to SLn may be arranged at an angle to the plurality of data lines DL1 to DLm and may cross the plurality of data lines DL1 to DLm. For example, the plurality of scan lines SL1 to SLn may be perpendicular to the plurality of data lines DL1 to DLm The type of the display panel 10 is not particularly limited to a particular type of display device. For example, the display panel 10 may be a self-luminous display panel such as an organic light emitting display panel. Alternatively, the display panel 10 may include a liquid crystal display (LCD) panel, an electro-phoretic display (EPD) panel, or an electro-wetting display (EWD) panel, and the like. When the display panel 10 is a non-luminescent display panel, the display device 1 may further include a back-light unit (BLU) for supplying light to the display panel 10.

In an exemplary embodiment of the present invention, the display panel 10 may include the sensor array SAR including biometric information sensors 100. For example, a plurality of biometric information sensors 100 may be arranged in the sensor array area SAR (e.g., in a matrix configuration). The biometric information sensors 100 may operate in an ultrasonic manner. In addition, a conduction line (e.g., a conductive pattern) may be connected to the sensor array SAR to transfer an ultrasonic wave generating signal or a detection signal between the biometric information sensors 100 and the sensor driver 30.

In an exemplary embodiment of the present invention, the biometric information sensors 100 may be arranged in non-light emitting areas between the pixels PX. As an example, the biometric information sensors 100 may include a plurality of sensors PS. Each of the sensors PS may be in position adjacent to a corresponding pixel PX. For example, a sensor PS may be positioned between two adjacent pixels PX at opposite sides of the sensor PS from each other. As an example, the pixels PX may be arranged in rows or columns, which are spaced apart from each other, and a corresponding row or column of sensors PS may be positioned between an adjacent row or column of pixels PX.

According to an exemplary embodiment of the present invention, each of the sensors PS may be a fingerprint sensor. Each of the fingerprint sensors PS may be included in a fingerprint sensor array, which may be arranged as described in more detail above.

According to an exemplary embodiment of the present invention, the fingerprint sensors PS in the fingerprint sensor array may each be an ultrasonic transmitter or an ultrasonic receiver, as described in more detail below.

The biometric information sensor 100 may be a sensor for detecting and identifying the characteristic of a user such as the fingerprint, the iris, the shape of the bone, or the skin. The biometric information sensor 100 may operate in the ultrasonic manner. The biometric information sensor 100 may include a fingerprint sensor. Thus, the biometric information sensor 100 may be interchangeably referred to as a fingerprint sensor 100 herein. As an example, the fingerprint sensor 100 may be an ultrasonic fingerprint sensor. However, this is an example, and the fingerprint sensor 100 may be replaced or applied by a sensor for detecting an iris, a skin, or a bone (e.g., according to an object to be detected).

The display driver 20 may be electrically connected to the display panel 10. The display driver 20 may apply signals for driving the display panel 10. For example, the display driver 20 may include at least one of a scan driver 22, a data driver 24, or a timing controller 26 for driving the scan driver 22 and the data driver 24. In an exemplary embodiment of the present invention, at least one of the scan driver 22, the data driver 24, and the timing controller 26 may be integrated in one display driver IC (D-IC). However, the arrangement of the drivers is not limited thereto. For example, at least one of the scan driver 22, the data driver 24, and the timing controller 26 may be integrated or mounted on the display panel 10.

The scan driver 22 may apply a scan signal to the scan lines SL1 to SLn based on a first control signal CONT1 provided from the timing controller 26.

The data driver 24 may apply a data signal (or a data voltage) to the data lines DL1 based on a data control signal DCS and image data RGB provided from the timing controller 26. The data driver 24 may be integrated on a flexible printed circuit board (FPC) attached to (e.g., mounted on) a substrate of the display panel 10. As an example, the data driver 24 may be in direct contact with the substrate of the display panel 10.

The timing controller 26 may receive an RGB image signal, a vertical synchronization signal, a horizontal synchronization signal, a main clock signal, or a data enable signal from an external graphic controller, and may generate the first control signal CONT1, the data control signal DCS, and the image data RGB corresponding to the RGB image signal based on the received signals. The timing controller 26 may provide the first control signal CONT1 to the scan driver 22 and provide the image data RGB and the data control signal DCS to the data driver 24.

The sensor driver 30 may control driving of the sensor array SAR. In an exemplary embodiment of the present invention, the sensor driver 30 may output the ultrasonic wave generating signal for generating ultrasonic waves of the fingerprint sensor 10, and may receive the detection signal to detect the fingerprints (or the biometric information) of the user. The detection signal may be generated in the fingerprint sensor 100 by using reflected ultrasonic waves. The information detected by the sensor driver 30 may be provided to the timing controller 26 or an external processor so that driving such as user authentication may be performed.

Referring to FIG. 2, the sensor array SAR (e.g., a fingerprint sensor array) may include a plurality of fingerprint sensors 100. The fingerprint sensors 100 may be arranged in a matrix form. The fingerprint sensors 100 may each include an ultrasonic transmitter and/or an ultrasonic receiver.

The fingerprint sensor 100 may operate as at least one of the ultrasonic transmitter for generating the ultrasonic wave or the ultrasonic receiver for receiving the ultrasonic wave reflected from a specific portion of the user's body to generate a detection signal. In an exemplary embodiment of the present invention, some of the fingerprint sensors 100 may be configured as the ultrasonic transmitter and others as the ultrasonic receivers. In an exemplary embodiment of the present invention, each of the fingerprint sensors 100 may be variably operated as the ultrasonic transmitter or the ultrasonic receiver depending on the situation.

The fingerprint sensor 100 may detect the shape of the fingerprint based on a touch, an approach, or a pressure, in which may be applied in a first direction DR1. For example, a charge transfer (or an electric field) in a second direction DR2 three-dimensionally perpendicular to the first direction DR1 may be generated by a touch in the first direction DR1. As an example, the second direction DR2 and a third direction DR3 perpendicular to the second direction DR2 may define a plane, and an upper surface of the display panel 10 may extend along the plane defined by the second direction DR2 and the third direction DR3. The first direction DR1 may be orthogonal to the second direction DR2 and the third direction DR3. As an example, contact may be made between a user's fingertip with the display panel 10 along the first direction DR1. For example, the contact may be made with an uppermost surface of the display panel 10. Additionally, pressure may be applied by the user's fingertip to the display panel 10 (e.g. with the uppermost surface of the display panel) along the first direction DR1.

Each of the fingerprint sensors 100 may include a first sensor electrode 120, a second sensor electrode 140, and a piezoelectric layer 160. The piezoelectric layer 160 may be disposed between the first sensor electrode 120 and the second sensor electrode. For example, the piezoelectric layer 160 may be in direct contact with a surface of the first sensor electrode 120 facing the second sensor electrode 140, and the piezoelectric layer 160 may also be in direct contact with a surface of the second sensor electrode 140 facing the first sensor electrode 120.

The first sensor electrode 120 and the second sensor electrode 140 may be disposed on a same layer (e.g., a same layer positioned at a same distance on or above an underlying substrate). The first sensor electrode 120 and the second sensor electrode 140 may be formed on the substrate by a single electrode patterning process. For example, the first sensor electrode 120 and the second sensor electrode 140 may include a same conductive material as each other.

In an exemplary embodiment of the present invention, the first sensor electrode 120 and the second sensor electrode 140 included in one fingerprint sensor 100 may be spaced apart from each other in the second direction DR2. Accordingly, the charge transfer may occur between the first sensor electrode 120 and the second sensor electrode 140 in the second direction DR2 or the opposite direction thereto. However, the directions and shapes of the first sensor electrode 120 and the second sensor electrode 140 are not limited thereto. For example, the first sensor electrode 120 and the second sensor electrode 140 may be arranged in the third direction DR3 perpendicular to the second direction DR2. As an example, the first sensor electrode 120 may be spaced apart from the second sensor electrode 140 in the third direction DR3, and the piezoelectric layer 160 may be disposed between the first sensor electrode 120 and the second sensor electrode 140 spaced apart in the third direction DR3.

In an exemplary embodiment of the present invention, the first sensor electrode 120 may be connected to a conduction line or a conductive pattern (e.g., a conduction line CH11, CH12, CH13, CH21, CH22, or CH23 described below in more detail) transmitting a common voltage VC. For example, the first sensor electrode 120 may provide a reference voltage for electromotive force generation or charge transfer generation. In an exemplary embodiment of the present invention, the common voltage VC may be provided to a cathode electrode of the pixel PX. However, this is an example, and the common voltage VC is not limited thereto. For example, the common voltage VC may be a ground voltage or a DC voltage provided from a separate voltage source.

The second sensor electrode 140 may be connected to a conduction line (e.g., conduction line CH11, CH12, CH13, CH21, CH22, or CH23) for transmitting an ultrasonic wave generating signal UGS or a detection signal SEN.

When the ultrasonic wave generating signal UGS output from the sensor driver 30 is applied to the fingerprint sensor 100 through the second sensor electrode 140, the piezoelectric material (e.g., piezoelectric layer) 160 may be vibrated and the ultrasonic wave may be generated. For example, the piezoelectric layer 160 may include a piezoelectric material. Thus, the fingerprint sensor 100 may operate as the ultrasonic transmitter.

In an exemplary embodiment of the present invention, the fingerprint sensor 100 that receives the reflection of ultrasonic waves due to a user's touch, or pressurization (e.g., pressure being applied to the fingerprint sensor 100) may cause the charge transfer in a horizontal direction of the substrate (e.g., a horizontal direction of the sensor array SAR). For example, the charge transfer may occur along the second direction DR2 or the third direction DR3. The detection signal SEN may be generated by the electromotive force between the first sensor electrode 120 and the second sensor electrode 140. The detection signal SEN may be provided to the sensor driver 30 through the conduction line (e.g., CHI). Thus, the fingerprint sensor 100 may operate as the ultrasonic receiver.

In an exemplary embodiment of the present invention, amplifiers (e.g., amplifier AMP) for amplifying the ultrasonic wave generating signal UGS and/or the detection signal SEN may be coupled to the conduction lines CH11, C12, CH13, CH21, CH22, and CH23, respectively, which may increase the detection sensitivity.

In an exemplary embodiment of the present invention, the piezoelectric layer 160 may be disposed between a sidewall of the first sensor electrode 120 and a sidewall of the second sensor electrode 140 adjacent to the sidewall of the first sensor electrode 120. An electrical signal may be converted into a mechanical vibration by the piezoelectric layer 160 to generate ultrasonic waves. The detection signal SEN may be generated as the piezoelectric layer 160 receiving the ultrasonic wave reflection vibrates.

In an exemplary embodiment of the present invention, the fingerprint sensors 100 operating as the ultrasonic transmitter may be activated in a time-series manner (e.g., sequentially) in accordance with the output sequence of the ultrasonic wave generating signal USG provided to the sensor array SAR arranged in a matrix form. In an exemplary embodiment of the present invention, the ultrasonic wave generating signal USG may be substantially simultaneously provided to the fingerprint sensors 100 operating as the ultrasonic transmitter, so that the fingerprint detection operation may be performed on the entire sensor array SAR at the same time. In an exemplary embodiment of the present invention, the fingerprint sensors 100 may be selectively activated by selectively providing the ultrasonic generating signal USG to the fingerprint sensors 100 depending on the position at which a finger touches a particular fingerprint sensor 100.

Since the biometric information sensor such as the fingerprint sensor 100 in the ultrasonic manner may include the first and second sensor electrodes 120 and 140 formed by a single conductive layer pattern, the sensor array SAR manufacturing process may be simplified and the manufacturing cost may be reduced. Further, thinning of the sensor array SAR may be realized. Thus, the display panel 10 including the relatively thin sensor array SAR including the fingerprint sensors 100 described herein may be included in a bendable, foldable or curved display panel, and such a display panel may be manufactured at relatively low cost.

Figure 3:
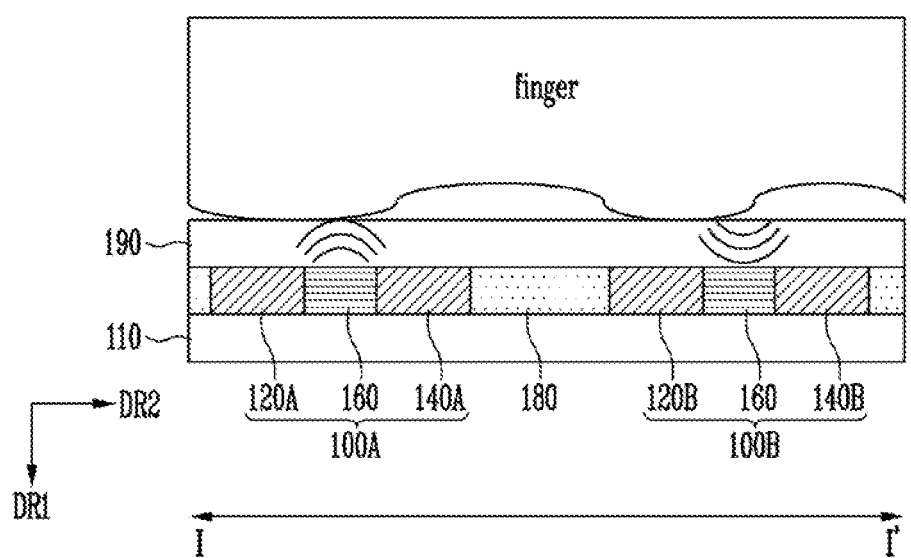
FIG. 3 is a cross-sectional view taken along section line I-I' of FIG. 2.

FIG. 3 is a cross-sectional view taken along section line I-I' of FIG. 2.

Referring to FIGS. 2 and 3, fingerprint sensors 100A and 100B may each include a first substrate 110, first sensor electrodes 120A and 120B, second sensor electrodes 140A and 140B, the piezoelectric layer 160, and a second substrate 190.

The fingerprint sensors 100A and 100B may detect the characteristics of an object (for example, a finger of a user) approaching or touching the display device 1 in the first direction DR1 (for example, a Z axis direction, which may be a direction orthogonal to the upper surface of the first substrate 110) perpendicular to the first substrate 110.

The first substrate 110 may include a transparent plastic material. In an exemplary embodiment of the present invention, the first substrate 110 may include a transparent resin substrate having flexibility. However, this is an example, and the first substrate 110 may be a transparent rigid substrate. In one example, the first substrate 110 may include polyimide.

The first sensor electrodes 120A and 120B may be patterned and disposed on the first substrate 110. The first sensor electrodes 120A and 120B may be electrically connected to a conduction line transmitting the common voltage to operate as a reference electrode for generating an ultrasonic wave, or a detection signal SEN. For example, the first sensor electrodes 120A and 120B may be directly connected to the conduction line transmitting the common voltage.

The first sensor electrodes 120A and 120B may be formed by patterning a first conductive member. In an exemplary embodiment of the present invention, the first sensor electrodes 120A and 120B (e.g., the first conductive member) may include a transparent conductive material. For example, the first sensor electrodes 120A and 120B may include at least one of indium tin oxide (ITO), indium zinc oxide (IZO), zinc oxide (ZnO), indium tin zinc oxide (ITZO), PEDOT, metal nanowire, or graphene. In an exemplary embodiment of the present invention, the first sensor electrodes 120A and 120B may have a metal conductive layer. For example, the first sensor electrodes 120A and 120B may include at least one of molybdenum, silver, titanium, copper, aluminum, or an alloy of at least two thereof. For example, the metal conductive layer may include an alloy of titanium and aluminum.

The second sensor electrodes 140A and 140B may be disposed on a same layer as the first sensor electrodes 120A and 120B on the first substrate 110. For example, the second sensor electrodes 140A and 140B and the first sensor electrodes 120A and 120B may each be in direct contact with the substrate 100. The second sensor electrodes 140A and 140B and the first sensor electrodes 120A and 120B may each be positioned a same distance above the first substrate 110 from each other (e.g., along the first direction DR1). Upper and/or lower surfaces of each of the second sensor electrodes 140A and 140B and the first sensor electrodes 120A and 120B may be aligned with each other. The second sensor electrodes 140A and 140B may be spaced apart from the first sensor electrodes 120A and 120B. For example, the second sensor electrodes 140A and 140B may be spaced apart from the first sensor electrodes 120A and 120B in the second direction DR2 (e.g., an X-axis direction, which may be parallel to an upper surface of the substrate 110). However, this is an example, and the directions in which the first sensor electrodes 120A and 120B and the second sensor electrodes 140A and 140B are arranged apart from each other are not limited thereto. For example, the first sensor electrodes 120A and 120B and the second sensor electrodes 140A and 140B may be disposed apart from each other in the Y-axis direction, or may be disposed diagonally apart from each other in the X-axis.

The second sensor electrodes 140A and 140B may be formed by patterning a second conductive member. In an exemplary embodiment of the present invention, the second sensor electrodes 140A and 140B may include a same material as the first sensor electrodes 120A and 120B. For example, the first sensor electrodes 120A and 120B and the second sensor electrodes 140A and 140B may be formed by a single patterning process on a conductive member.

The conventional ultrasonic sensor has a structure in which the first and second sensor electrodes are stacked in the first direction DR1, which may be the direction perpendicular to an upper surface the substrate, with the piezoelectric material therebetween. For example, the conventional ultrasonic sensor may have a structure in which a plurality of conductive pattern layers are sequentially deposited along the first direction DR1, thus limiting the thinness of the ultrasonic sensor. In addition, a deposition (or patterning)

process for depositing a plurality of conductive pattern layers must be performed more than once.

However, the fingerprint sensors 100A and 100B according to an exemplary embodiment of the present invention may include the first and second sensor electrodes 120A, 120B, 140A, and 140B patterned in the horizontal direction (e.g., in the second direction DR2) on the first substrate 110, and thus the thicknesses of the fingerprint sensors 100A and 100B may be reduced. As the fingerprint sensors 100A and 100B are thinned, the fingerprint sensors 100A and 100B may be integrated with the display device and may be applied to flexible (e.g., or foldable) electronic devices. Further, since the sensor electrodes may be formed by only one conductive patterning process, the manufacturing process may be simplified and the manufacturing cost may be greatly reduced.

The piezoelectric layer 160 may be disposed between a sidewall of each of the first sensor electrodes 120A and 120B and a sidewall of each of the second sensor electrodes 140A and 140B adjacent thereto. The piezoelectric layer 160 may be in contact with the sidewalls of the first sensor electrodes 120A and 120B and the sidewalls of the second sensor electrodes 140A and 140B adjacent thereto.

The piezoelectric layer 160 may include a transparent organic material having piezoelectric characteristics or a transparent inorganic material having piezoelectric characteristics. Thus, the piezoelectric layer 160 may be interchangeably referred to herein as a piezoelectric material layer. As an example, the piezoelectric layer 160 may include a polyvinylidene fluoride (PVDF) based piezoelectric material as the organic material, or may include a piezoelectric ceramic material as the inorganic material. Examples of the piezoelectric ceramic material may include lead zirconate titanate (PZT), zinc oxide (ZnO), barium titanate (BaTiO3), or aluminum nitride (AlN).

In an exemplary embodiment of the present invention, the piezoelectric layer 160 may be disposed between the first sensor electrodes 120A and 120B and the second sensor electrodes 140A and 140B, respectively, but might not be disposed in areas other than between the first sensor electrodes 120A and 120B and the second sensor electrodes 140A and 140B, respectively. For example, the piezoelectric layer 160 might not be disposed between the fingerprint sensors 100A and 100B. However, this is an example, and the arrangement of the piezoelectric layer 160 is not limited thereto. A planarization layer 180 may be filled between the different fingerprint sensors 100A and 100B. In an exemplary embodiment of the present invention, the planarization layer 180 may include an organic insulation layer or an inorganic insulation layer. In an exemplary embodiment of the present invention, the planarization layer 180 may include a same material as the piezoelectric material layer 160. In an exemplary embodiment of the present invention, the area in which the planarization layer 180 (see, e.g., FIG. 3) may be an area in a vacuum state without the planarization layer 180. Thus, the space between the fingerprint sensors 100A and 100B may be an empty space in a vacuum state.

The first sensor electrodes 120A and 120B, the second sensor electrodes 140A and 140B, and the piezoelectric layer 160 may have substantially a same height as each other. Thus, the thickness of the fingerprint sensors 100A and 100B can be minimized.

The height of the first sensor electrodes 120A and 120B and the height of the second sensor electrodes 140A and 140B may be controlled to control areas of opposite sides of the first sensor electrodes 120A and 120B and the second sensor electrodes 140A and 140B. Oscillation (e.g., ultrasonic wave transmission) and ultrasonic wave reception characteristics may be controlled according to the height of the first sensor electrodes 120A and 120B and the height of the second sensor electrodes 140A and 140B.

The piezoelectric layer 160 may be formed by a coating process on the first substrate 110 on which the first sensor electrodes 120A and 120B and the second sensor electrodes 140A and 140B are patterned. Thereafter, an annealing process for heating the piezoelectric layer 160 to a high temperature for a predetermined period of time and/or a polling process for applying a high-voltage to the piezoelectric layer 160 for a relatively short time may be performed to increase the piezoelectric characteristics of the piezoelectric layer 160.

The piezoelectric layer 160 may be vibrated by an electrical signal to generate an ultrasonic wave or the electrical detection signal SEN may be generated by the vibration of the piezoelectric layer 160 by ultrasonic wave reflection. For example, the charge transfer in the second direction DR2 may occur in the piezoelectric material layer 160 included in the ultrasonic receiver due to the pressure in the first direction DR1, and an electric signal (e.g., the detection signal SEN) may be generated. Thus, biometric information such as a fingerprint can be detected.

In an exemplary embodiment of the present invention, the first fingerprint sensor 100A may operate as the ultrasonic transmitter and the second fingerprint sensor 100B may operate as the ultrasonic receiver; however, exemplary embodiments of the present invention are not limited thereto. For example, the first fingerprint sensor 100A may operate as the ultrasonic receiver and the second fingerprint sensor 100B may operate as the ultrasonic transmitter. Referring to FIG. 3, the first fingerprint sensor 100A may be the ultrasonic transmitter that generates ultrasonic waves, and the second fingerprint sensor 100B may be the ultrasonic receiver that receives reflected ultrasonic waves. However, this is an example, and the first and second fingerprint sensors 100A and 100B may be variable sensors whose ultrasonic wave reception and transmission roles are variable. For example, the ultrasonic wave reception and transmission roles may vary depending on the signals provided to the second sensor electrodes 140A and 140B or the conduction line connected to the second sensor electrodes 140A and 140B.

The second substrate 190 may be disposed on the first sensor electrodes 120A and 120B, the second sensor electrodes 140A and 140B, and the piezoelectric layer 160. The second substrate 190 may substantially cover the first sensor electrodes 120A and 120B, the second sensor electrodes 140A and 140B, and the piezoelectric layer 160. In an exemplary embodiment of the present invention, the second substrate 190 may include a transparent resin having flexibility or a glass. In an exemplary embodiment of the present invention, the second substrate 190 may be in a positioned and dimensioned to correspond to a base substrate (e.g., substrate 110) of the display panel. As an example, the fingerprint sensors 100A and 100B may be disposed on (e.g., attached to) a lower portion of the display panel.

According to an exemplary embodiment of the present invention, the second substrate 190 may be in insulation layer. Thus, the second substrate 190 may be referred to as an insulation layer 190 herein.

As described above, the fingerprint sensors 100A and 100B according to an exemplary embodiment of the present invention may include first and second sensor electrodes 120A, 120B, 140A, and 140B arranged in parallel on the same layer by a single conductive member, and thus the manufacturing process may be simplified and the manufacturing cost may be reduced.

In addition, thinning of the fingerprint sensors 100A and 100B included in the display device may be realized. Accordingly, the fingerprint sensors 100A and 100B and the display panel may be integrally formed, or the fingerprint sensors 100A and 100B may be formed inside the display panel.

FIGS. 4 to 8 are each cross-sectional views illustrating an example of a biometric information sensor according to an exemplary embodiment of the present invention.

Duplicative descriptions of components that are substantially the same or similar to those described above with reference to FIGS. 1-3 may be omitted below with reference to FIGS. 4 to 8. The biometric information sensor will be described as a fingerprint sensor below with reference to FIGS. 4 to 8 as an example; however, exemplary embodiments of the present invention are not limited thereto.

Referring to FIGS. 4 to 8, fingerprint sensors 101A, 102A, 103A, 104A, 105A, 101B, 102B, 103B, 104B and 105B may each include the first substrate 110, the first sensor electrodes 120A and 120B, the second sensor electrodes 140A and 140B, and the second substrate 190. Piezoelectric layers 161, 162, 163, 164 and 165 may be respectively included in the fingerprint sensors 101A, 102A, 103A, 104A, 105A, 101B, 102B, 103B, 104B and 105B, as described below in more detail.

A structure of the fingerprint sensor may be described in more detail below with reference to the fingerprint sensors 101A, 102A, 103A, 104A, or 105A. The fingerprint sensors 101B, 102B, 103B, 104B and 105B may respectively have substantially the same or similar configuration to the fingerprint sensors 101A, 102A, 103A, 104A, or 105A.

The first sensor electrodes 120A and 120B and the second sensor electrodes 140A and 140B may be disposed in parallel to each other on a same layer above the first substrate 110. For example, each of the first sensor electrodes 120A and 120B and the second sensor electrodes 140A and 140B may be in direct contact with the substrate 110. As an example, the first sensor electrodes 120A and 120B and the second sensor electrodes 140A and 140B may be spaced apart from the substrate 110 at a same distance from each other (e.g., in the first direction DR1)

Figure 4:
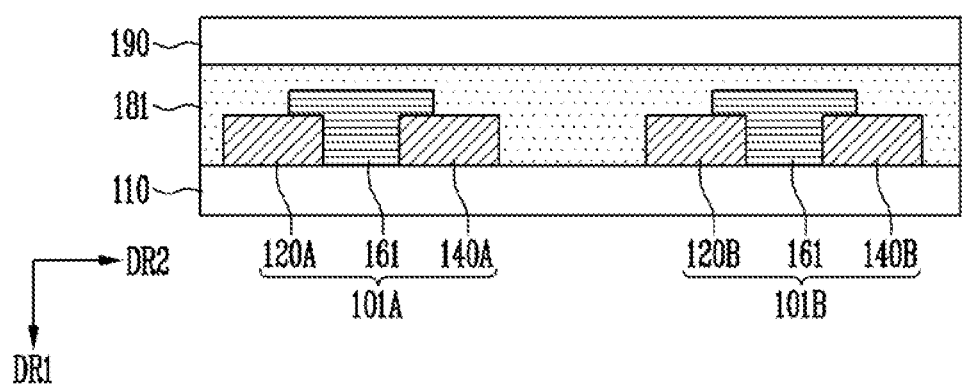
FIGS. 4 to 8 are each cross-sectional views illustrating an example of a biometric information sensor according to an exemplary embodiment of the present invention.

Referring to FIG. 4, in an exemplary embodiment of the present invention, the piezoelectric layer 161 may be disposed between the first sensor electrode 120A and the second sensor electrode 140A adjacent to the first sensor electrode 120A. The piezoelectric layer 161 may cover at least a part of an upper surface of the first sensor electrode 120A and at least a part of an upper surface of the second sensor electrode 140A. For example, a height (e.g., a thickness in the first direction D1) of the piezoelectric layer 161 may be greater than the height of the first sensor electrode 120A and the second sensor electrode 140A. Accordingly, the charge transfer effect between the first sensor electrode 120A and the second sensor electrode 140A may be increased.

In an exemplary embodiment of the present invention, the piezoelectric material might not be disposed between the fingerprint sensors 101A and 101B, which might eliminate electrical interference between the fingerprint sensors 101A and 101B.

In an exemplary embodiment of the present invention, a planarization layer 181 may be disposed on the first sensor electrode 120A, the second sensor electrode 140A, and the piezoelectric material layer 161 to flatten upper portions of the first sensor electrode 120A, the second sensor electrode 140A, and the piezoelectric material layer 161. The second substrate 190 may be disposed (e.g., deposited) on the planarization layer 181. The second substrate 190 may be in direct contact with the planarization layer 181. In an exemplary embodiment of the present invention, the planarization layer 181 may include at least one of an inorganic insulating material or an organic insulating material. In an exemplary embodiment of the present invention, the planarization layer 181 may include a same material as the piezoelectric material layer 161.

Figure 5:
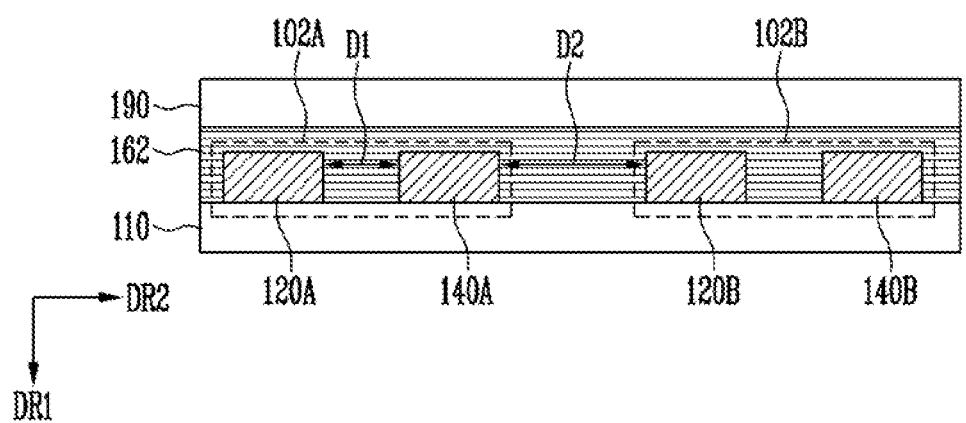

Referring to FIG. 5, the piezoelectric layer 162 may be formed to cover at least a portion of the first substrate 110 and the first and second sensor electrodes 120A, 120B, 140A, and 140B. For example, the piezoelectric layer 162 may be disposed on portions of the substrate 110 that are not covered by the first and second sensor electrodes 120A, 120B, 140A, and 140B, and may cover side and upper surfaces of the first and second sensor electrodes 120A, 120B, 140A, and 140B. For example, the piezoelectric layer 162 may be formed by spin coating on the first substrate 110 on which the first and second sensor electrodes 120A, 120B, 140A, and 140B are patterned. A distance D1 between the first sensor electrode 120A and the second sensor electrode 140A included in the fingerprint sensor 102A may be shorter than the shortest distance D2 between the fingerprint sensors 102A and 102B adjacent to each other. For example, the distance D2 between the fingerprint sensors 102A and 102B may be set to reduce or eliminate the influence of the vibration or electric effect (e.g., an electric field) of the piezoelectric layer 162 on the adjacent fingerprint sensors 102A and 102B. The shortest distance D2 between the adjacent fingerprint sensors 102A and 102B may be a distance between the nearest sensor electrodes between the adjacent fingerprint sensors 102A and 102B. For example, the shortest distance D2 may be a straight-line distance between the second sensor electrode 140A of the first fingerprint sensor 102A and the first sensor electrode 120B of the second fingerprint sensor 102B.

Accordingly, the fingerprint sensor 102A according to an exemplary embodiment of the present invention described with reference to FIG. 5 may be formed by processes from which the patterning process of the piezoelectric layers 160 and 161 and/or the deposition process of the planarization layer 181 in the fingerprint sensor 100A and 101A described with reference to FIGS. 3 and 4 are omitted. Therefore, the manufacturing process of the fingerprint sensor 102A may be further simplified.

Figure 6:
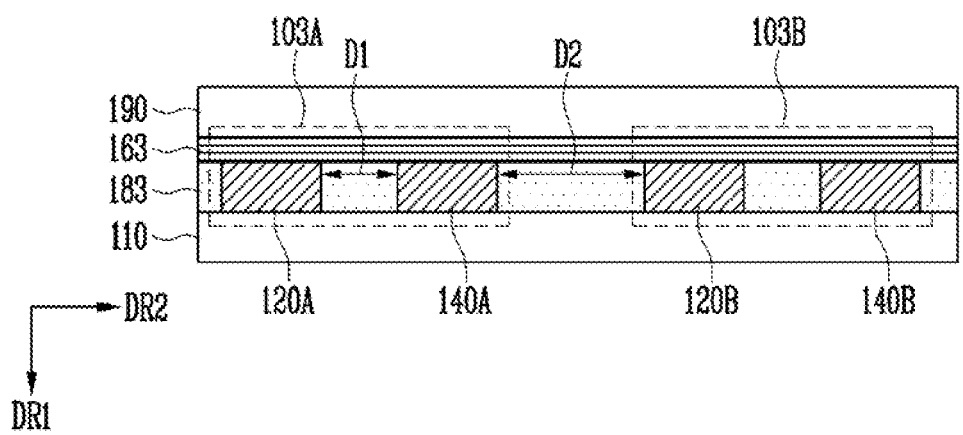

In an exemplary embodiment of the present invention, referring to FIG. 6, the piezoelectric layer 163 may be formed (e.g., may be integrally formed) on the upper surfaces of the first and second sensor electrodes 120A and 140A. An insulation layer pattern 183 may be disposed between the first and second sensor electrodes 120A and 140A and between adjacent first and second fingerprint sensors 103A and 103B. The distance D1 between the first sensor electrode 120A and the second sensor electrode 120B may be shorter than the shortest distance D2 between the adjacent fingerprint sensors 103A and 103B, which may reduce or eliminate the influence of the vibration or electric effect of the piezoelectric layer 163 on the adjacent fingerprint sensors 103A and 103B. The piezoelectric layer 163 connecting the first and second sensor electrodes 120A and 140A of the fingerprint sensor 103A may have a substantially uniform thickness, and thus the uniformity of ultrasonic wave detection may be increased.

Figure 7:
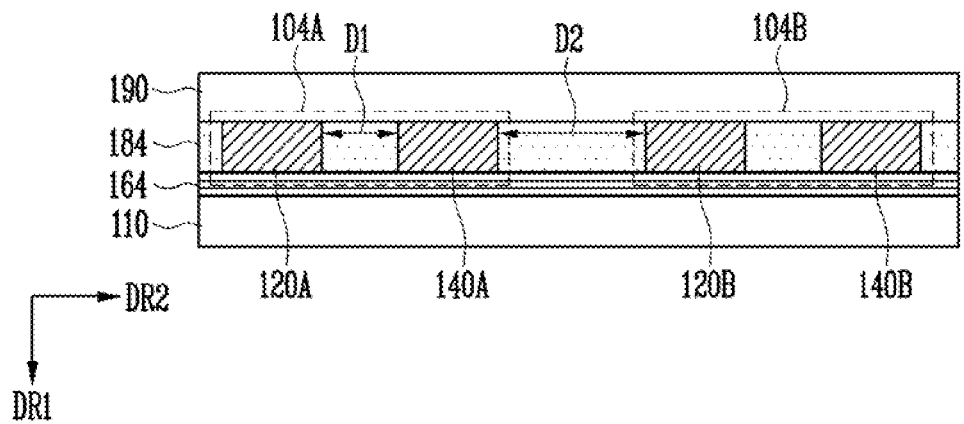

In an exemplary embodiment of the present invention, referring to FIG. 7, a piezoelectric layer 164 may be formed (e.g., may be integrally formed) under the lower surface of the first and second sensor electrodes 120A and 140A.

An insulation layer pattern 184 may be disposed between the first and second sensor electrodes 120A and 140A, between the first and second sensor electrodes 120B and 120B, and between adjacent first and second fingerprint sensors 104A and 104B. The distance D1 between the first sensor electrode 120A and the second sensor electrode 120B may be shorter than the shortest distance D2 between the adjacent fingerprint sensors 104A and 104B, which may reduce or eliminate an influence of the vibration or electric effect of the piezoelectric layer 164 on the adjacent fingerprint sensors 104A and 104B. When the piezoelectric layer 164 connecting the first and second sensor electrodes 120A and 140A of the fingerprint sensor 104A or the piezoelectric layer 164 connecting the first and second sensor electrodes 120B and 140B has a substantially uniform thickness, the uniformity of ultrasonic wave detection may be increased.

According to an exemplary embodiment of the present invention, the insulation layer pattern 184 may be disposed on side surfaces of each of the first sensor electrode 120A, the second sensor electrode 140A, the first sensor electrode 120B and the second sensor electrode 140B. For example, the insulation layer pattern 184 may be disposed between the second substrate 190 and the piezoelectric layer 164. The insulation layer pattern 184 may be in direct contact with a bottom surface of the second substrate 190 facing the first substrate 110 and may be in direct contact with a top surface of the piezoelectric layer 164 facing the second substrate 190.

Figure 8:
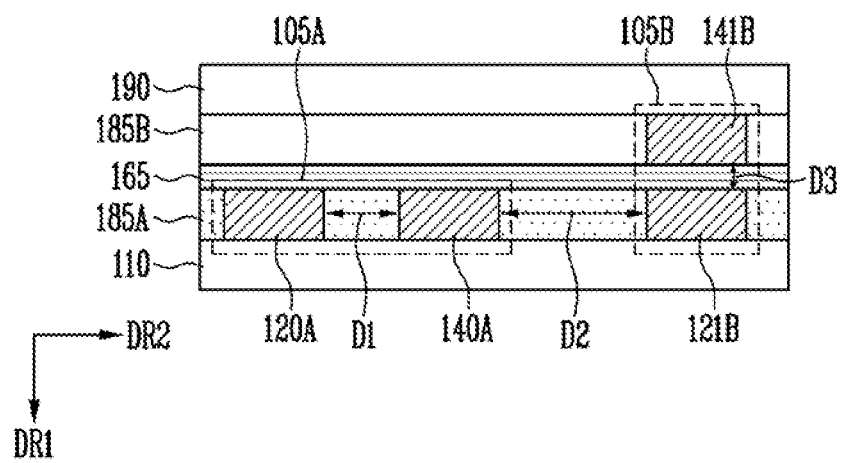

In an exemplary embodiment of the present invention, referring to FIG. 8, the fingerprint sensors may include a first fingerprint sensor 105A formed in the second direction DR2, along an extending direction (e.g., along an upper surface of) the first substrate 110, and a second fingerprint sensor 105B stacked in the first direction DR1 perpendicular to the second direction DR2.

The first fingerprint sensor 105A may include the first sensor electrode 120A, the second sensor electrode 140A disposed in parallel on the first substrate 110, and a piezoelectric layer 165 that substantially covers the first and second sensor electrodes 120A and 140A (e.g., integrally). For example, the piezoelectric layer 165 may substantially cover upper surfaces of the first and second sensor electrodes 120A and 140A facing the second substrate 190. According to an exemplary embodiment of the present invention, the piezoelectric layer 165 may have a substantially uniform thickness (e.g., in the first direction DR1).

According to an exemplary embodiment of the present invention, a first insulation layer pattern 185A may be disposed on an upper surface of the first substrate 110 facing the second substrate 190. The first insulation layer pattern 185A may be disposed between the first and second sensor electrodes 120A and 140A and may be in direct contact with side surfaces of the first and second sensor electrodes 120A and 140A. The first insulation layer pattern 185A may also be in direct contact with side surfaces of a third sensor electrode 121B described in more detail below.

According to an exemplary embodiment of the present invention, a second insulation layer pattern 185B may be disposed on the piezoelectric layer 165. For example, the second insulation layer pattern 185B may be in direct contact with an upper surface of the piezoelectric layer 165 facing the second substrate 190. The second insulation layer pattern 185B may substantially cover the upper surface of the piezoelectric layer 165 facing the second substrate 190. The second insulation layer pattern 185B may also be in direct contact with side surfaces of a fourth sensor electrode 141B described in more detail below.

The second fingerprint sensor 105B may include the third sensor electrode 121B spaced apart from the first and second sensor electrodes 120A and 140A (e.g., along the second direction DR2). The third sensor electrode 121B may be disposed on a same layer as the first and second sensor electrodes 120A and 140A (e.g., may be positioned at a same distance from the substrate 110). The third sensor electrode 121B may be formed by substantially the same patterning process as that of the first and second sensor electrodes 120A and 140B. The piezoelectric layer 165 may cover substantially the entire upper surface of the third sensor electrode 121B.

The second fingerprint sensor 105B may further include the fourth sensor electrode 141B overlapping the third sensor electrode 121B on the piezoelectric layer 165 (e.g., along the first direction DR1). A distance D3 between the third sensor electrode 121B and the fourth sensor electrode 141B may be shorter than the shortest distance D2 between the adjacent fingerprint sensors 105A and 105B such that the influence of the vibration or the electric effect of the piezoelectric layer 165 on the adjacent fingerprint sensors 105A and 105B may be reduced or eliminated.

The first fingerprint sensor 105A may generate the charge transfer in the second direction DR2 and the second fingerprint sensor 105B may generate the charge transfer in the first direction DR1 when a touch by a finger is made in the first direction DR1. Since the intensity of the electric field in the direction parallel to the direction of the force (e.g., the intensity of the electric field by the second fingerprint sensor 105B) may act 10 times or more than the intensity of the electric field in the direction perpendicular to the direction of the force (e.g., the intensity of the electric field by the first fingerprint sensor 105A), the detection reliability (e.g., sensitivity) by the second fingerprint sensor 105B may be higher than the detection reliability by the first fingerprint sensor 105A.

For example, the first fingerprint sensor 105A may be an ultrasonic transmitter, and the second fingerprint sensor 105B may be an ultrasonic receiver. Thus, the detection sensitivity can be increased.

Figure 9:
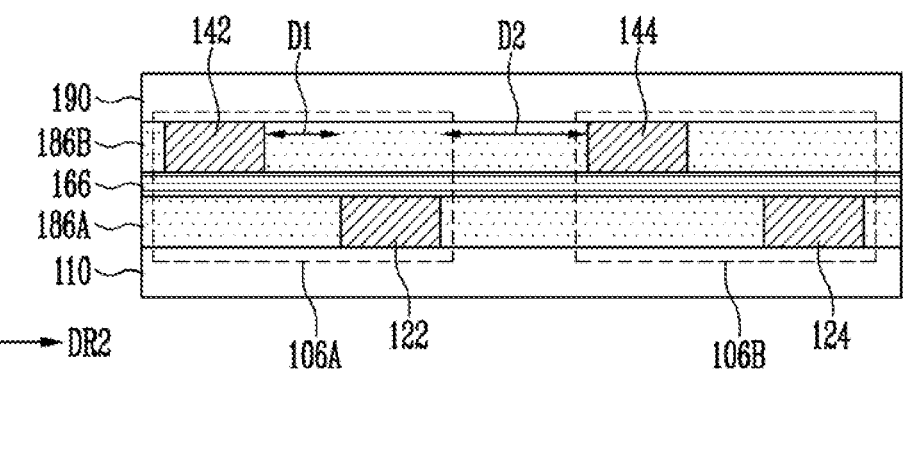
FIG. 9 is a cross-sectional view illustrating an example of a biometric information sensor according to an exemplary embodiment of the present invention.

FIG. 9 is a cross-sectional view illustrating an example of a biometric information sensor according to an exemplary embodiment of the present invention.

Duplicative descriptions of components that are substantially the same or similar to those described above with reference to FIGS. 1-3 may be omitted below with reference to FIG. 9. The biometric information sensor will be described as a fingerprint sensor below with reference to FIG. 9 as an example; however, exemplary embodiments of the present invention are not limited thereto.

Referring to FIG. 9, a first fingerprint sensor 106A may include a first sensor electrode 122, a piezoelectric layer 166, and a third sensor electrode 142 and a second fingerprint sensor 106B may include a second sensor electrode 124, the piezoelectric layer 166, and a fourth sensor electrode 144.

The first sensor electrode 122 and the second sensor electrode 124 may be disposed on the first substrate 110 and spaced apart from each other. The first sensor electrode 122 and the second sensor electrode 124 may be in direct contact with the first substrate 110. The first sensor electrode 122 and the second sensor electrode 124 may be different fingerprint sensors.

A first planarization layer 186A may be disposed on the first substrate 110 on which the first sensor electrode 122 and the second sensor electrode 124 are patterned. The first planarization layer 186A may be in direct contact with the substrate 110 (e.g., in areas of the substrate 110 that are not in direct contact with the first sensor electrode 122 and the second sensor electrode 124) and may be in direct contact with side surfaces of first sensor electrode 122 and the second sensor electrode 124. The piezoelectric layer 166 may be disposed on the first planarization layer 186A. The piezoelectric layer 166 may be integrally formed on the first planarization layer 186A.

The third sensor electrode 142 and the fourth sensor electrode 144 may be disposed on the piezoelectric layer 166 and spaced apart from each other (e.g., in the second direction DR2. The third sensor electrode 142 and the fourth sensor electrode 144 do not overlap with the first and second sensor electrodes 122 and 124. A second planarization layer 186B may be disposed on the piezoelectric layer 166 on which the third sensor electrode 142 and the fourth sensor electrode 144 are patterned. The second planarization layer 186B may be in direct contact with portion of the piezoelectric layer 166 not in direct contact with the third sensor electrode 142 and the fourth sensor electrode 144. The second planarization layer 186B may be in direct contact with side surfaces of the third sensor electrode 142 and the fourth sensor electrode 144.

When a pressure in the first direction DR1 perpendicular to the first substrate 110 is applied to the first substrate 110, the charge transfer may occur between the first sensor electrode 122 and the third sensor electrode 142 in the second direction DR2 parallel to the first substrate 110. For example, the first sensor electrode 122 and the third sensor electrode 142 may form one fingerprint sensor 106A (e.g., the ultrasonic transmitter or the ultrasonic receiver).

Similarly, the charge transfer may occur between the second sensor electrode 124 and the fourth sensor electrode 144 in the second direction DR2. For example, the second sensor electrode 124 and the fourth sensor electrode 144 may form another fingerprint sensor 106B (e.g., the ultrasonic transmitter or the ultrasonic receiver).

Figure 10:
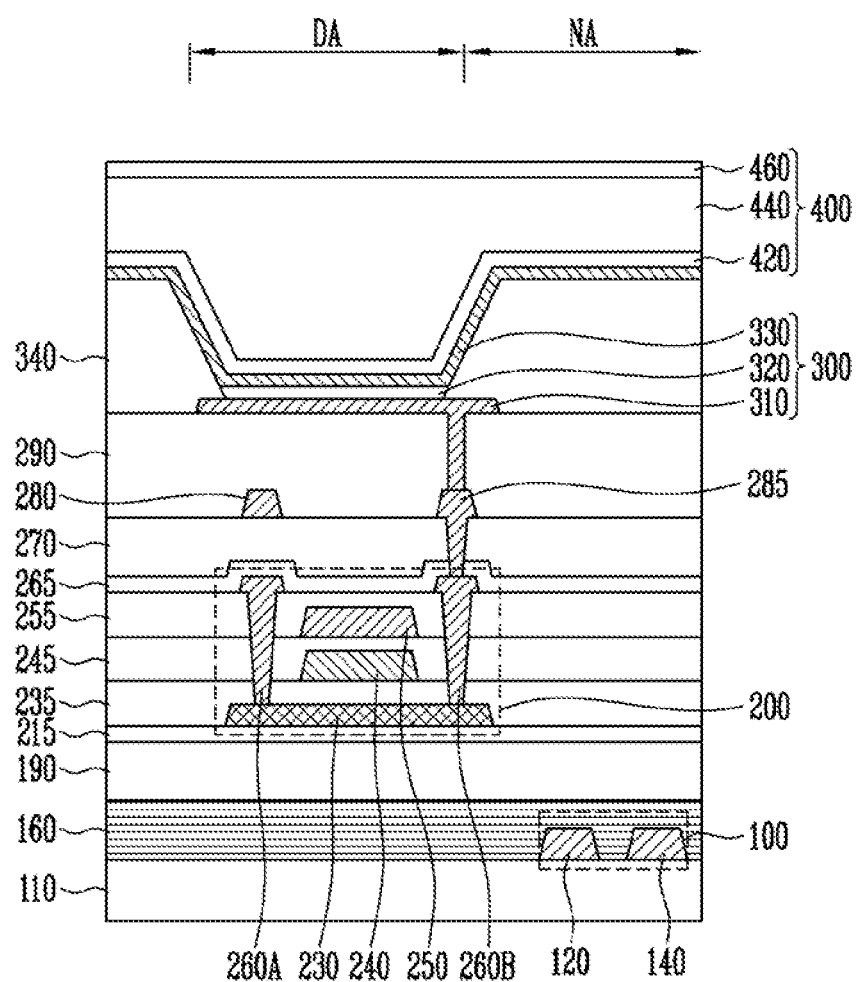
FIG. 10 is a cross-sectional view illustrating an example of the display device of FIG. 1.

FIG. 10 is a cross-sectional view illustrating an example of the display device of FIG. 1.

Referring to FIGS. 1, 2, and 10, the display device may include the substrate 110, the fingerprint sensor array having the fingerprint sensors 100, the insulation layer 190, a backplane structure, a pixel structure 300, and an encapsulation layer 400.

In an exemplary embodiment of the present invention, the second substrate 190 may be an insulation layer including an insulation material. Thus, the substrate 190 may be interchangeably referred to herein as insulation layer 190. Thus, the insulation layer 190 may be substantially the same as or similar to the second substrate 190 described above with reference to FIGS. 3 to 9.

Duplicative descriptions of the fingerprint sensor 100 described in more detail above with reference to FIGS. 1 to 9 may be omitted below. Further, technical features described above with reference to FIGS. 1 to 9 may be applicable to the exemplary embodiments of the present invention described below with reference to FIG. 10.

The substrate 110 may include a transparent resin substrate having flexibility. For example, the substrate may include a polyimide-based resin. Alternatively, the substrate 110 may be a rigid substrate.

The fingerprint sensor 100 may include the first sensor electrode 120, the second sensor electrode 140, and the piezoelectric layer 160 disposed between the first and second sensor electrodes 120 and 140. The first sensor electrode 120 may be disposed between the substrate 110 and the insulation layer 190. The second sensor electrode 140 may be disposed on a same layer as the first sensor electrode 120. For example, the sensor electrodes 120 and 140 may each be disposed on (e.g., may be in direct contact with) substrate 110.

The first sensor electrode 120 may be electrically connected to the common voltage and the second sensor electrode 140 may be connected to a conduction line for transmitting the ultrasonic wave generating signal or the detection signal.

The fingerprint sensor 100 may operate as the ultrasonic transmitter or the ultrasonic receiver. When the ultrasonic wave generating signal is transmitted through the second sensor electrode 140, the fingerprint sensor comprising the first sensor electrode 120, the second sensor electrode 140, and the piezoelectric layer 160 may operate as the ultrasonic transmitter to generate ultrasonic waves. In an exemplary embodiment of the present invention, when the ultrasonic wave generating signal is not transmitted through the second sensor electrode 140 of the fingerprint sensor, the corresponding fingerprint sensor 100 may operate as the ultrasonic receiver to generate the detection signal.

Although the first and second sensor electrodes 120 and 140 might not be in direct contact with the insulation layer 190, the first and second sensor electrodes 120 and 140 are not limited thereto. For example, the first and second sensor electrodes 120 and 140 may be in direct contact with the insulation layer 190. For example, upper surfaces of the first and second sensor electrodes 120 and 140 facing the insulation layer 190 may be in direct contact with a bottom surface of the insulation layer 190 facing the substrate 110.

The insulation layer 190 may be disposed on the first sensor electrode 120, the second sensor electrode 140, and the piezoelectric layer 160. The insulation layer 190 may block electrical influences between the backplane structure and the fingerprint sensor 100. For example, the insulation layer 190 may reduce or eliminate electrical influences between the semiconductor element 200 and the biometric information sensor (e.g., fingerprint sensor) 100. In an exemplary embodiment of the present invention, the insulation layer 190 may include a transparent resin substrate having flexibility. For example, the substrate may include a polyimide-based resin. In an exemplary embodiment of the present invention, the insulation layer 190 may have a form in which a plurality of transparent organic insulation layers and a plurality of transparent inorganic insulation layers are alternately (e.g., and repeatedly) stacked.

A buffer layer 215 may be disposed on the insulation layer 190. For example, the buffer layer 215 may be in direct contact with an upper surface of the insulation layer 190 facing way from the substrate 110. The buffer layer 215 may be disposed entirely on the substrate 110 corresponding to the substrate 110. For example, the buffer layer 115 may cover substantially an entire upper surface of the insulation layer 190. The buffer layer 215 may prevent the diffusion of metal atoms or impurities from the insulation layer 190 to a semiconductor element 200 and may control the rate of heat transfer during the crystallization process to form an active layer 230. In addition, the buffer layer 215 may increase the flatness of a surface of the insulation layer 190 (e.g., when a surface, such as the upper surface, of the insulation layer 190 is not uniform).

The backplane structure including the semiconductor element 200 may be disposed on the buffer layer 215. For example, the semiconductor element 200 may be in direct contact with an upper surface of the buffer layer 215 facing away from the second substrate 190. The backplane structure may include a thin film transistor for driving the pixel, a capacitor, and wirings. An example configuration of the backplane structure is described in more detail below.

An active layer 230 may be disposed on the buffer layer 215. The active layer 230 may include an oxide semiconductor, an inorganic semiconductor (e.g., amorphous silicon, or poly silicon), or an organic semiconductor.

A gate insulating layer 235 may be disposed on the active layer 230. The gate insulating layer 235 may have a substantially flat upper surface without forming a step around the active layer 230 while substantially covering the active layer 230, or may be disposed with a substantially uniform thickness (e.g., in the first direction DR1) along a profile of the active layer 230. The gate insulating layer 235 may include a silicon compound, or a metal oxide.

A first gate electrode 240 may be disposed on the gate insulating layer 235 and may overlap the active layer 230 (e.g., in the first direction DR1). The first gate electrode 240 may include a metal, an alloy, a metal nitride, a conductive metal oxide, or a transparent conductive material. These may be used alone or in combination with each other.

A first insulating interlayer 245 may be disposed on the first gate electrode 240. The first insulating interlayer 245 may have a substantially flat upper surface without forming a step around the first gate electrode 240 while substantially covering the first gate electrode 240, or may be disposed with a substantially uniform thickness (e.g., in the first direction DR1) along a profile of the gate electrode 240. The first insulating interlayer 245 may include a silicon compound, or a metal oxide.

A second gate electrode 250 may be disposed on the first insulating interlayer 245 and may overlap the first gate electrode 240 (e.g., in the first direction DR1). The second gate electrode 250 may include a metal, an alloy, a metal nitride, a conductive metal oxide, or a transparent conductive material. These may be used alone or in combination with each other.

A second insulating interlayer 255 may be disposed on the second gate electrode 250. The second insulating interlayer 255 may substantially cover the second gate electrode 250. The second insulating interlayer 255 may have a substantially flat upper surface without forming a step around the second gate electrode 250, or may be disposed with a substantially uniform thickness (e.g., in the first direction DR1) along the profile of the gate electrode 250. The second insulating interlayer 255 may include a silicon compound, or a metal oxide.

The gate insulating layer 235, the first insulating interlayer 245, and the second insulating interlayer 255 may be collectively referred to as an insulating layer structure.

A source electrode 260A and a drain electrode 260B may be disposed on the second insulating interlayer 255. The source electrode 260A may be connected to a source region of the active layer 230 through a predetermined first contact hole formed in the insulating layer structure and the drain electrode 260B may be connected to a predetermined second contact hole formed in the insulating layer structure. The source electrode 260A and the drain electrode 260B may each include a metal, an alloy, a metal nitride, a conductive metal oxide, or a transparent conductive material. These may be used alone or in combination with each other. Accordingly, the semiconductor element 200 including the active layer 230, the first gate electrode 240, the second gate electrode 250, the source electrode 260A, and the drain electrode 260B may be formed.

The semiconductor element 200 may have a top gate structure, but the structure of the semiconductor element 200 is not limited thereto. For example, the semiconductor element 200 may have a bottom gate structure.

A passivation layer 265 may be disposed on the source and drain electrodes 260A and 260B. The passivation layer 265 may be disposed with a substantially uniform thickness (e.g., in the first direction DR1) along the profile of the source and drain electrodes 260A and 260B to substantially cover the source and drain electrodes 260A and 260B. The passivation layer 265 may include a silicon compound, or a metal oxide.

A first planarization layer 270 may be disposed on the passivation layer 265. The first planarization layer 270 may have a substantially flat upper surface. The first planarization layer 270 may include an organic material or an inorganic material. In an exemplary embodiment of the present invention, the planarization layer 270 may include an organic material.

A wiring pattern (e.g., line pattern) 280 and a connection pattern 285 may be disposed on the first planarization layer 270. The wiring pattern 280 may transmit a scan signal, a data signal, an initialization signal, or a power supply voltage. The connection pattern 285 may be connected to the drain electrode 260B through a contact hole. The connection pattern 285 may electrically connect a lower electrode 310 of the pixel structure 300 and the drain electrode 260B. The wiring pattern 280 and the connection pattern 285 may include a metal, an alloy, a metal nitride, a conductive metal oxide, or a transparent conductive material. These may be used alone or in combination with each other.

A second planarization layer 290 substantially covering the wiring pattern 280 and the connection pattern 285 may be disposed on the first planarization layer 270. The second planarization layer 290 may have a substantially planar (e.g., flat) upper surface. The second planarization layer 290 may include an organic material or an inorganic material.

The pixel structure 300 may be disposed on the backplane structure. The pixel structure 300 may correspond to a light emitting region and may include the lower electrode 310, an organic light emitting layer 320, and an upper electrode 330. The pixel structure 300 may be at least partially separated from the neighboring pixel structures by a pixel defining layer 340.

The lower electrode 310 may be disposed on the second planarization layer 290. The lower electrode 310 may be connected to the connection pattern 285 through the contact hole and may be electrically connected to the semiconductor element 200. The lower electrode 310 may include a metal, an alloy, a metal nitride, a conductive metal oxide, or a transparent conductive material. These may be used alone or in combination with each other.

The pixel defining layer 340 may be disposed on the second planarization layer 290 to expose a portion of the lower electrode 310. The organic light emitting layer 320 may be disposed on the exposed portion of the lower electrode 310. The pixel defining layer 340 may include an organic material or an inorganic material.

The organic light emitting layer 320 may be disposed on the lower electrode 310 partially exposed by the pixel defining layer 340. The organic light emitting layer 320 may be formed using at least one of light emitting materials emitting light of different colors (e.g., red light, green light, or blue light) depending on the pixels. Alternatively, the organic light emitting layer 320 may emit white light as a whole by laminating a plurality of light emitting materials generating light of different colors such as red light, green light, or blue light. A color filter may be disposed on the organic light emitting layer 320. The color filter may include at least one of a red color filter, a green color filter, or a blue color filter. The color filter may include a yellow color filter, a cyan color filter, or a magenta color filter. The color filter may each include a photosensitive resin.

An upper electrode 330 may substantially entirely cover the pixel defining layer 340 and the organic light emitting layer 320. The upper electrode 330 may include a metal, an alloy, a metal nitride, a conductive metal oxide, or a transparent conductive material. These may be used alone or in combination with each other.

The encapsulation layer 400 may be disposed on the upper electrode 330. The encapsulation layer 400 may include a first thin encapsulation layer 420, a second thin encapsulation layer 440, and a third thin encapsulation layer 440.

The first thin film encapsulation layer 420 may substantially cover the upper electrode 330 and may be disposed along the profile of the upper electrode 330 with a substantially uniform thickness (e.g., in the first direction DR1). The first thin film encapsulation layer 420 may prevent the pixel structure 300 from being deteriorated due to penetration of moisture, or oxygen, for example. In addition, the first thin film encapsulation layer 420 may also protect the pixel structure 300 from an external impact. The first thin film encapsulation layer 420 may include inorganic materials.

The second thin film encapsulation layer 440 may be disposed on the first thin film encapsulation layer 420. The second thin film encapsulation layer 440 may increase the flatness of the display device 1 and protect the pixel structure 300. The second thin film encapsulation layer 440 may include organic materials.

A third thin film encapsulation layer 460 may be disposed on the second thin encapsulation layer 440. The third thin film encapsulation layer 460 may also protect the pixel structure 300 from an external impact. The third thin film encapsulation layer 460 may include inorganic materials.

The encapsulation layer 400 may have a laminated structure. The encapsulation layer 400 may include a lowermost layer and an uppermost layer, each including an inorganic layer or an organic layer. The encapsulation layer 400 may include organic layers and inorganic layers that are alternately (e.g., and repeatedly) stacked.

In the pixel structure 300, a region corresponding to the organic light emitting layer 320 may correspond to a light emitting area DA, and a region around the light emitting area DA, for example, a region in which the pixel defining layer 340 is disposed, may correspond to a non-light emitting area NA. The ultrasonic waves may be deformed by the conductive material, and the organic light emitting materials included in the organic light emitting layer 320 may emit light unintentionally by ultrasonic waves. In an exemplary embodiment of the present invention, the fingerprint sensor 100 may be disposed over the non-light emitting area NA, which may prevent deformation and the unintended emissions described above.

However, this is an example, and the arrangement position of the fingerprint sensor 100 is not limited thereto. The fingerprint sensor 100 overlapping the non-light emitting area NA may be embedded in the backplane structure, in the pixel defining layer 340, or in the touch sensor structure above the encapsulation layer 400. Further, the fingerprint sensor array including the fingerprint sensors 100 disposed under the insulation layer 190 and internal fingerprint sensors disposed in the backplane structure or the pixel defining layer 340 might not overlap with each other (e.g., in the first direction DR1).

Thus, the fingerprint sensor array including the fingerprint sensor 100 may be disposed directly below the display panel including the backplane structure and the pixel structure 300.

When the fingerprint sensor 100 includes a single conductive layer, thinning of the fingerprint sensor array can be realized and/or a fingerprint sensor integrated display device can be realized. Therefore, it is possible to manufacture a foldable and/or bendable display device including the fingerprint sensor 100. In addition, the manufacturing cost of the display device including the fingerprint sensor 100 may be reduced.

According to an exemplary embodiment of the present invention, referring, for example, to FIGS. 1-6 and 10, a display device may include the first substrate 110 and the biometric information sensor 100 disposed on the first substrate 110. The biometric information sensor 100 may include a first fingerprint sensor (e.g., fingerprint sensor 102A) and a second fingerprint sensor (e.g., fingerprint sensor 102b) spaced apart from the first fingerprint sensor. The first fingerprint sensor may include a first sensor electrode (e.g., sensor electrode 120A) in direct contact with the first substrate 110 and a second sensor electrode (e.g., sensor electrode 140A) in direct contact with the first substrate 110 and spaced apart from the first sensor electrode. The second fingerprint sensor may include a third sensor electrode (e.g., sensor electrode 120B) in direct contact with the first substrate 110 and a fourth sensor electrode (e.g., sensor electrode 140B) in direct contact with the first substrate 110 and spaced apart from the third sensor electrode. The piezoelectric layer 160 may be disposed on the first substrate 110 between the first and second sensor electrodes and between the third and fourth sensor electrodes. The second substrate 190 may be disposed on the piezoelectric layer 160. The semiconductor element 200 may be positioned above the second substrate 190.

In an exemplary embodiment of the present invention, a distance (e.g., distance D1) between the first and second sensor electrodes may be smaller than a distance (e.g., distance D2) between the first fingerprint sensor and the second fingerprint sensor.

FIGS. 11A, 11B, 11C and 11D are each cross-sectional views illustrating an example of the display device of FIG. 1.

Duplicative descriptions of components that are substantially the same or similar to those described above with reference to FIGS. 1-3 and/or FIG. 10 may be omitted below with reference to FIGS. 11A, 11B, 11C and 11D. The display device described below with reference to FIGS. 11A to 11D may be substantially the same or similar to the display device described above with reference to FIG. 10 except for an arrangement (e.g., position) of the fingerprint sensor 100. Further, technical features described above with reference to FIGS. 1 to 9 may be applicable to the exemplary embodiments of the present invention described below with reference to FIGS. 11A to 11D.

Referring to FIGS. 11A to 11D, the display device may include a substrate 195, the fingerprint sensor array having the fingerprint sensors 100, the insulation layer 190, the backplane structure, the pixel structure 300, and the encapsulation layer 400.

In an exemplary embodiment of the present invention, the semiconductor element 200 and the fingerprint sensor 100 may be included in the backplane structure. The fingerprint sensor 100 may be disposed in the non-light emitting area NA.

The substrate 195 may include a transparent resin substrate having flexibility. For example, the substrate 195 may include the polyimide-based resin. Alternatively, the substrate 195 may be a rigid substrate.

Figure 11A:
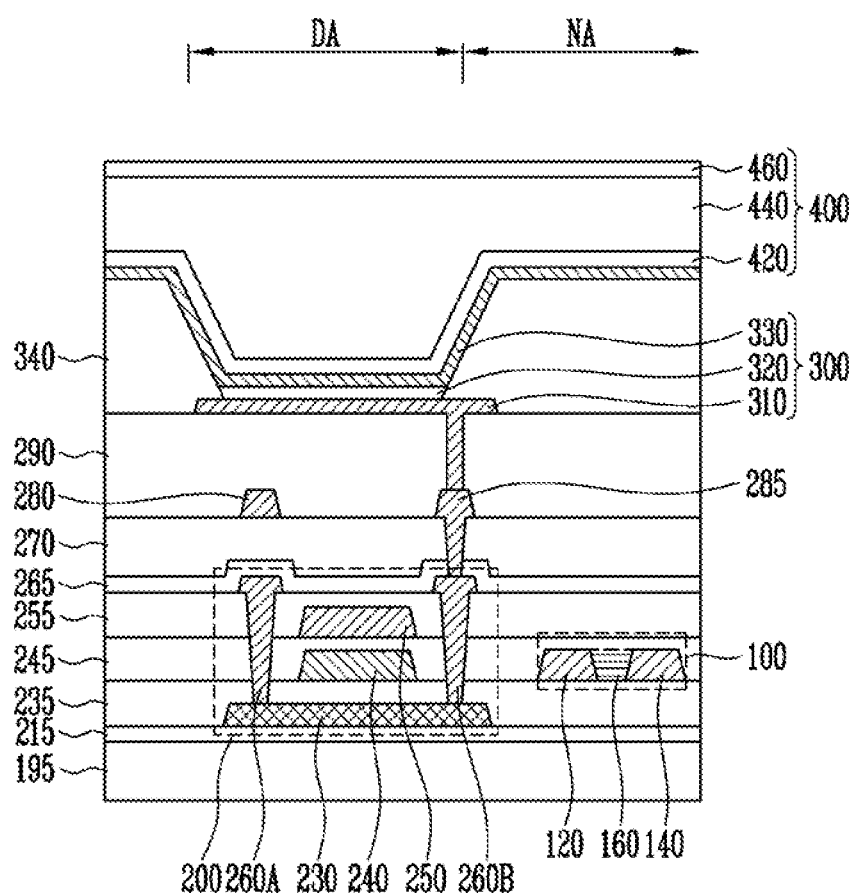

Referring to FIG. 11A, in an exemplary embodiment of the present invention, the first and second sensor electrodes 120 and 140 of the fingerprint sensor 100 may be disposed on a same layer as the first gate electrode 240. For example, the first and second sensor electrodes 120 and 140 of the fingerprint sensor 100 and the first gate electrode 240 may each be positioned at a same distance from the substrate 195. For example, the first and second sensor electrodes 120 and 140 and the first gate electrode 240 may be formed by one conductive layer patterning process. The piezoelectric layer 160 may be disposed between the first and second sensor electrodes 120 and 140. In an exemplary embodiment of the present invention, the first insulating interlayer 245 substantially covering the first gate electrode 240 may include a same material as the piezoelectric material layer 160. For example, the first insulating interlayer 245 and the piezoelectric layer 160 may be formed by a single deposition process.

Accordingly, the fingerprint sensor array including the fingerprint sensor 100 may also be formed by the processes of forming the first gate electrode 240 and the first insulating interlayer 245. Therefore, the fingerprint sensor 100 may be embedded inside the display device, the manufacturing process for forming the fingerprint sensor 100 may be simplified, and the manufacturing cost can be reduced.

Referring to FIG. 11B, in an exemplary embodiment of the present invention, the first and second sensor electrodes 120 and 140 of the fingerprint sensor 100 may be disposed on a same layer as the second gate electrode 250. For example, the first and second sensor electrodes 120 and 140 of the fingerprint sensor 100 and the second gate electrode 250 may each be positioned at a same distance from the substrate 195. For example, the first and second sensor electrodes 120 and 140 and the second gate electrode 250 may be formed by one conductive layer patterning process. In an exemplary embodiment of the present invention, the second insulating interlayer 255 substantially covering the second gate electrode 250 may include a same material as the piezoelectric material layer 160. For example, the second insulating interlayer 255 and the piezoelectric layer 160 may be formed by a single deposition process.

In an exemplary embodiment of the present invention, the first and second sensor electrodes 120 and 140 of the fingerprint sensor 100 and the source and drain electrode 260A and 260B may be formed on a same layer by a single conductive layer patterning process.

Referring to FIG. 11C, in an exemplary embodiment of the present invention, the first and second sensor electrodes 120 and 140 of the fingerprint sensor 100 may be disposed on a same layer as the wiring pattern 280. For example, the first and second sensor electrodes 120 and 140 of the fingerprint sensor 100 and the wiring pattern 280 may each be positioned at a same distance from the substrate 195. For example, the first and second sensor electrodes 120 and 140 and the wiring pattern 280 may be formed by one conductive layer patterning process. In an exemplary embodiment of the present invention, the planarization interlayer 290 substantially covering the second gate electrode 250 may include a same material as the piezoelectric material layer 160. For example, the planarization interlayer 290 and the piezoelectric layer 160 may be formed by a single deposition process.

Figure 11D:
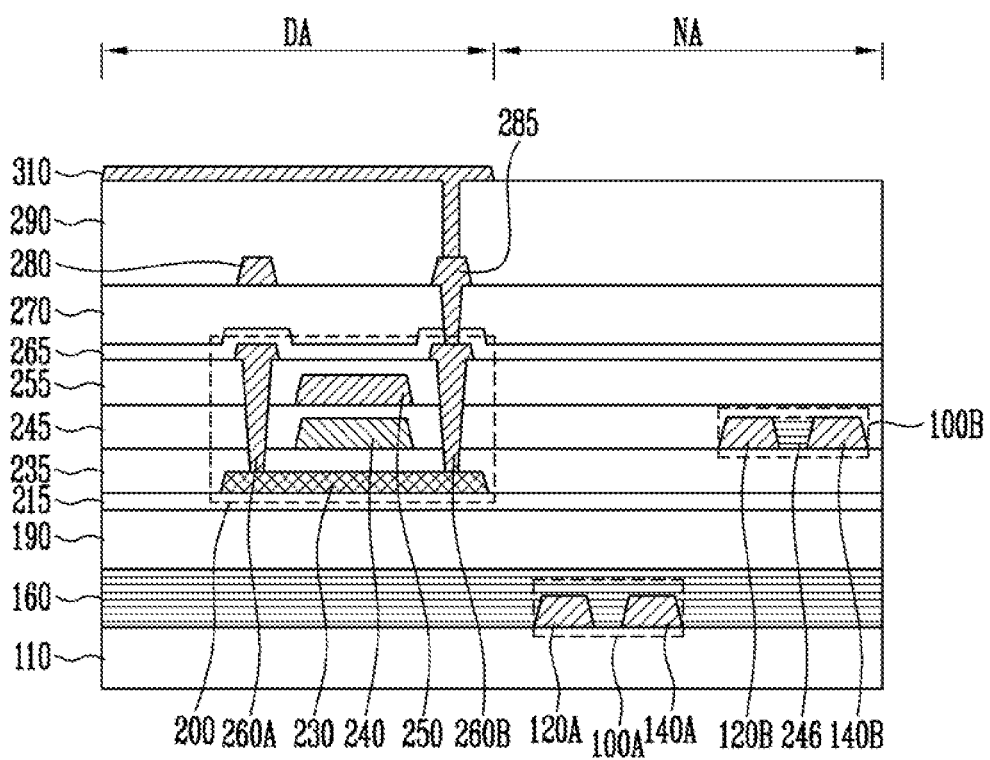

Referring to FIG. 11D, in an exemplary embodiment of the present invention, the fingerprint sensors 100A and 100B may be disposed in a plurality of layers. For example, the fingerprint sensors 100A and 100B may be disposed in different layers from each other, and may be spaced apart from each other along a direction orthogonal to an upper surface of the first substrate 110. The fingerprint sensors 100A and 100B may be arranged not to overlap with each other (e.g., along the first direction DR1, which may prevent unintended interference of ultrasonic waves generated in the display panel including the fingerprint sensors 100A and 100B).

The first fingerprint sensor 100A may be disposed in the non-light emitting area NA under the insulation layer 190. For example, a first fingerprint sensor array including the first fingerprint sensor 100A may be disposed under the insulation layer 190.

The second fingerprint sensor 100B may be disposed in the non-emission area NA in the backplane structure. For example, the second fingerprint sensor 100B may be formed on a same layer as the first gate electrode 240 (e.g., may be positioned at a same distance from substrate 195), and a second fingerprint sensor array including the second fingerprint sensor 100B may be arranged on the gate insulating layer 235.

According to an exemplary embodiment of the present invention, a second piezoelectric layer 246 may be positioned between the first sensor electrode 120B and the second sensor electrode 140B of the second fingerprint sensor 100B. For example, the second piezoelectric layer 246 may be in direct contact with side surfaces of the first sensor electrode 120B and the second sensor electrode 140B of the second fingerprint sensor 100B.

However, this is an example, and the arrangement of the fingerprint sensors is not limited thereto. For example, the fingerprint sensor may be arranged at various positions (e.g., depending on the wiring structure and the density of components included in the display panel).

As an example, when the fingerprint sensor array including the ultrasonic fingerprint sensor 100 is embedded in the backplane structure, the manufacturing cost may be reduced, and a foldable and/or bendable display device including the fingerprint sensor 100 may be manufactured.

Figure 12:
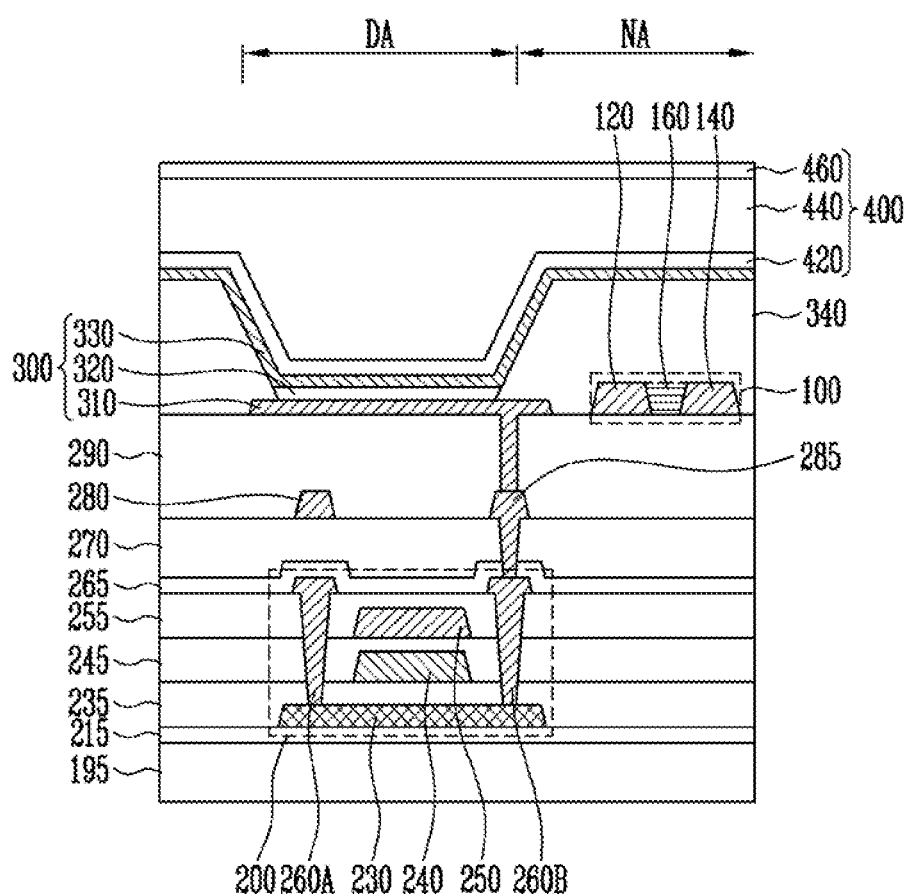
FIGS. 12 and 13 are each cross-sectional views illustrating an example of the display device of FIG. 1.
Figure 13:
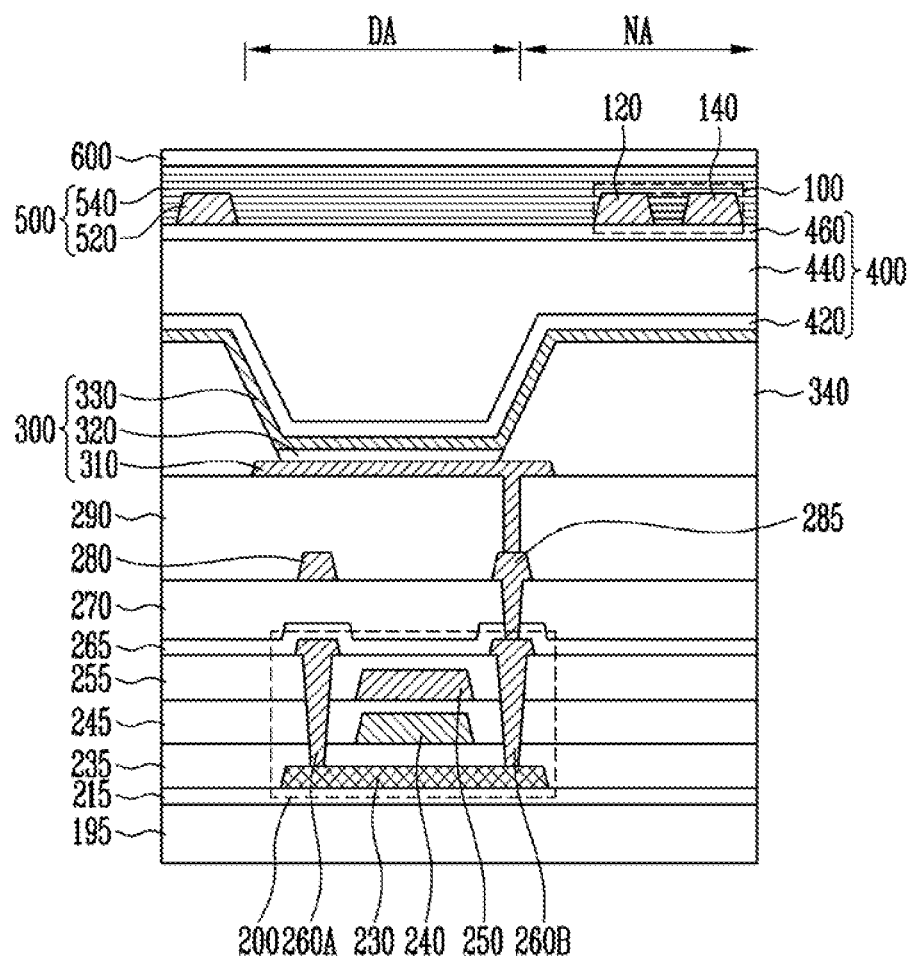

FIGS. 12 and 13 are each cross-sectional views illustrating an example of the display device of FIG. 1.

Duplicative descriptions of components that are substantially the same or similar to those described above with reference to FIGS. 1-3 and/or FIG. 10 may be omitted below with reference to FIGS. 12 and 13. The display device described below with reference to FIGS. 12 and 13 may be substantially the same or similar to the display device described above with reference to FIG. 10 except for an arrangement (e.g., position) of the fingerprint sensor 100. Further, technical features described above with reference to FIGS. 1 to 9 may be applicable to the exemplary embodiments of the present invention described below with reference to FIGS. 12 and 13.

Referring to FIGS. 12 and 13, the display device may include the substrate 195, the fingerprint sensor array having the fingerprint sensors 100, the insulation layer 190, the backplane structure, the pixel structure 300, and the encapsulation layer 400.

In an exemplary embodiment of the present invention, referring to FIG. 12, the fingerprint sensor 100 may be included within the pixel structure 300. The fingerprint sensor 100 may be disposed in the non-light emitting area NA. The first and second sensor electrodes 120 and 140 of the fingerprint sensor 100 may be disposed on a same layer as the lower electrode 310. For example, the first and second sensor electrodes 120 and 140 of the fingerprint sensor 100 and the lower electrode 310 may each be positioned at a same distance from the substrate 195. For example, the first and second sensor electrodes 120 and 140 and the lower electrode 310 may be formed by one conductive layer patterning process.

In an exemplary embodiment of the present invention, Referring to FIG. 13, the display device may further include a touch sensor structure 500 including a touch electrode pattern 520, a touch wiring, and an insulating structure 540 on the encapsulation layer 400. The display device may further include a protection layer 600 including a transparent material for protecting the lower structures on the touch sensor structure 500. In an exemplary embodiment of the present invention, the fingerprint sensor 100 may be disposed in the non-light emitting area NA within the touch sensor structure 500. The first and second sensor electrodes 120 and 140 of the fingerprint sensor 100 may be disposed on a same layer as the touch electrode pattern 520. For example, the first and second sensor electrodes 120 and 140 of the fingerprint sensor 100 and the touch electrode pattern 520 may each be positioned at a same distance from the substrate 195. For example, the first and second sensor electrodes 120 and 140 and the touch electrode pattern 520 may be formed by one conductive layer patterning process. In an exemplary embodiment of the present invention, the insulating structure 540 may include a piezoelectric material.

As an example, when the fingerprint sensor array including the ultrasonic fingerprint sensor 100 is embedded in the pixel structure 300 or the touch sensor structure 500, the manufacturing cost may be reduced, and a foldable and/or bendable display device including the fingerprint sensor 100 may be manufactured.

As an example, the ultrasonic biometric information sensor (e.g., the fingerprint sensor) and the display device having the same according to an exemplary embodiment of the present invention may include first and second sensor electrodes arranged in parallel on a same layer (e.g., on a single conductive member), and thus the sensor array manufacturing process may be simplified and the manufacturing cost may be reduced. In addition, thinning of the sensor array included in the display device may be realized. Accordingly, the fingerprint sensors and the display panel may be integrally formed, or the fingerprint sensors may be formed inside the display panel.

Further, as the thickness of the fingerprint sensor is reduced, the foldable and/or bendable display device including the fingerprint sensor can be manufactured with a reduced manufacturing cost.

Exemplary embodiments of the present invention may be applied to a biometric information sensor and a system including a display device. For example, exemplary embodiments of the present invention may be applied to a biometric information sensor detecting a fingerprint, an iris, a shape of a bone, a blood vessel, of skin.

While the present invention has been shown and described with reference to the exemplary embodiments thereof, it will be apparent to those of ordinary skill in the art that various changes in form and detail may be made thereto without departing from the spirit and scope of the present invention.

What is claimed is:

1. A biometric information sensor comprising:
   a first substrate;
   a first sensor electrode disposed on the first substrate;
   a second sensor electrode disposed on the first substrate at a same distance from the first substrate as the first sensor electrode and spaced apart from the first sensor electrode;
   a piezoelectric layer disposed between the first sensor electrode and the second sensor electrode; and
   a second substrate disposed on the first sensor electrode, the second sensor electrode, and the piezoelectric layer,
   wherein charge transfer occurs between the first sensor electrode and the second sensor electrode in a direction parallel to an upper surface of the first substrate facing the second substrate when a pressure is applied in a direction orthogonal to the upper surface of the first substrate.

2. The biometric information sensor of claim 1, wherein the piezoelectric layer covers at least a portion of an upper surface of the first sensor electrode and at least a portion of an upper surface of the second sensor electrode.

3. The biometric information sensor of claim 1, wherein heights of the piezoelectric layer, the first sensor electrode, and the second sensor electrode above the first substrate are substantially the same as each other.

4. The biometric information sensor of claim 1, wherein the first sensor electrode, the second sensor electrode, and the piezoelectric layer form an ultrasonic receiver generating a detection signal in response to a reflection of an ultrasonic wave.

5. The biometric information sensor of claim 4, wherein the first sensor electrode is electrically connected to a common voltage, and
   wherein the second sensor electrode is electrically connected to a conduction line transmitting the detection signal.

6. The biometric information sensor of claim 2, further comprising:
   a planarization layer disposed between the first sensor electrode, the second sensor electrode, and the piezoelectric layer and the second substrate to at least partially cover the first sensor electrode, the second sensor electrode, and the piezoelectric layer.

7. The biometric information sensor of claim 2, further comprising:
   a third sensor electrode disposed on the first substrate at a same distance from the first substrate as the first sensor electrode and spaced apart from the first and second sensor electrodes; and
   a fourth sensor electrode disposed on the piezoelectric layer to overlap the third sensor electrode,
   wherein the piezoelectric layer covers substantially an entire upper surface of the third sensor electrode.

8. The biometric information sensor of claim 7, wherein when the pressure is applied in the direction orthogonal to the upper surface of the first substrate facing the second substrate,
   charge transfer occurs in the direction orthogonal to the upper surface of the first substrate between the third sensor electrode and the fourth sensor electrode.

9. A display device comprising:
   a substrate;
   a fingerprint sensor array disposed on the substrate, the fingerprint sensor array including a plurality of fingerprint sensors having an ultrasonic transmitter and an ultrasonic receiver;

an insulation layer disposed on the fingerprint sensor array;
a semiconductor element disposed on the insulation layer;
a pixel structure disposed on the semiconductor element; and
an encapsulation layer disposed on the pixel structure,
wherein at least one of the fingerprint sensors comprises:
  a first sensor electrode disposed on the substrate;
  a second sensor electrode disposed on the substrate at a same distance from the substrate as the first sensor electrode, wherein the second sensor electrode is spaced apart from the first sensor electrode; and
  a piezoelectric layer disposed between the first sensor electrode and the second sensor electrode,
  wherein a distance between the first sensor electrode and the second sensor electrode is shorter than a shortest distance between adjacent fingerprint sensors of the plurality of fingerprint sensors.

10. The display device of claim 9, wherein the first sensor electrode is electrically connected to a common voltage, and
  wherein the second sensor electrode is electrically connected to a conduction line transmitting an ultrasonic wave generating signal or receiving a detection signal.

11. The display device of claim 10, wherein the piezoelectric layer covers at least a portion of an upper surface of the first sensor electrode and at least a portion of an upper surface of the second sensor electrode.

12. The display device of claim 10, wherein the ultrasonic transmitter and the ultrasonic receiver are disposed on a same layer.

13. The display device of claim 10, wherein at least one fingerprint sensor of the plurality of fingerprint sensors operates as an ultrasonic transmitter to generate an ultrasonic wave when the ultrasonic wave generating signal is transferred through the second sensor electrode.

14. The display device of claim 10, wherein at least one fingerprint sensor of the plurality of fingerprint sensors operates as an ultrasonic receiver to generate an ultrasonic wave when the ultrasonic wave generating signal is not transferred through the second sensor electrode.

15. The display device of claim 9, wherein the pixel structure includes an organic light emitting layer,
  wherein the pixel structure includes a light emitting area in a position corresponding to the organic light emitting layer and a non-light emitting area adjacent to the light emitting area, and
  wherein each of the fingerprint sensors overlaps the non-light emitting area.

16. The display device of claim 15, further comprising:
a second plurality of fingerprint sensors having substantially a same configuration as the plurality of fingerprint sensors of the fingerprint sensor array,
  wherein the second plurality of fingerprint sensors are arranged with the semiconductor element above the plurality of fingerprint sensors, and
  wherein the second plurality of fingerprint sensors do not overlap the fingerprint sensor array.

17. A display device comprising:
a substrate;
a semiconductor element disposed on the substrate;
a first sensor electrode disposed on the substrate;
a second sensor electrode disposed on the substrate at a same distance from the substrate as the first sensor electrode;
a piezoelectric material between the first sensor electrode and the second sensor electrode;
a pixel structure disposed on the semiconductor element, the pixel structure including a light emitting area and a non-light emitting area adjacent to the light emitting area; and
an encapsulation layer disposed on the pixel structure,
  wherein the first sensor electrode, the second sensor electrode, and the piezoelectric material form a fingerprint sensor, and
  wherein heights of uppermost surfaces of the piezoelectric material, the first sensor electrode, and the second sensor electrode above the substrate are substantially the same as each other.

18. The display device of claim 17, wherein the fingerprint sensor overlaps the non-light emitting area.

19. The display device of claim 18, wherein the first sensor electrode is electrically connected to a conduction line transmitting a common voltage, and
  wherein the second sensor electrode is electrically connected to a conduction line transmitting an ultrasonic wave generating signal or a detection signal.

20. A biometric information sensor comprising:
a first substrate;
a first sensor electrode disposed on the first substrate;
a second sensor electrode disposed on the first substrate at a same distance from the first substrate as the first sensor electrode, wherein the second sensor electrode is spaced apart from the first sensor electrode along a direction parallel to an upper surface of the first substrate facing the first sensor electrode;
a piezoelectric layer in direct contact with at least one surface of the first sensor electrode and at least one surface of the second sensor electrode, wherein the piezoelectric layer is spaced apart from lateral side surfaces of the first sensor electrode and the second sensor electrode; and
a second substrate disposed on the first sensor electrode, the second sensor electrode, and the piezoelectric layer.

21. The biometric information sensor of claim 20, wherein the piezoelectric layer covers at least a portion of an upper surface of the first sensor electrode and at least a portion of an upper surface of the second sensor electrode.

22. The biometric information sensor of claim 20, wherein the piezoelectric layer is integrally formed on an upper surface of the first sensor electrode and an upper surface of the second sensor electrode.

23. The biometric information sensor of claim 22, further comprising:
a third sensor electrode disposed on the first substrate at a same distance from the first substrate as the first sensor electrode, wherein the third sensor electrode is spaced apart from the first and second sensor electrodes; and
a fourth sensor electrode disposed on the piezoelectric layer.

24. The biometric information sensor of claim 23, wherein the fourth sensor electrode overlaps the third sensor electrode.

25. The biometric information sensor of claim 22, further comprising:
a third sensor electrode disposed on the piezoelectric layer not to overlap with the first and second sensor electrodes; and
a fourth sensor electrode disposed on the piezoelectric layer and spaced apart from the third sensor electrode, the fourth sensor electrode being not overlapped with the first and second sensor electrodes, wherein charge transfer occurs between the first sensor electrode and the third sensor electrode and between the second sensor electrode and the fourth sensor electrode along a first direction parallel to an upper surface of the first substrate when a pressure is applied in a second direction orthogonal to the upper surface of the first substrate.

26. The biometric information sensor of claim 20, wherein the piezoelectric layer is disposed between the first substrate and the first and second sensor electrodes and is in direct contact with a lower surface of each of the first and second sensor electrodes.

* * * * *